United States Patent [19]

Boger

[11] Patent Number: 4,743,584
[45] Date of Patent: * May 10, 1988

[54] C-TERMINAL AMIDE CYCLIC RENIN INHIBITORS CONTAINING PEPTIDE ISOSTERES

[75] Inventor: Joshua S. Boger, Westfield, N.J.

[73] Assignee: Merck & Co., Inc., Rahway, N.J.

[*] Notice: The portion of the term of this patent subsequent to Nov. 27, 2001 has been disclaimed.

[21] Appl. No.: 916,265

[22] Filed: Oct. 7, 1986

[51] Int. Cl.$^4$ .................. A61K 37/43; C07K 5/12
[52] U.S. Cl. ................................. 514/11; 530/317
[58] Field of Search .................... 530/317; 514/11

[56] References Cited

U.S. PATENT DOCUMENTS

| | | | |
|---|---|---|---|
| 4,185,096 | 1/1980 | Castro et al. | 514/19 |
| 4,216,209 | 8/1980 | Bellini et al. | 514/18 |
| 4,269,827 | 5/1981 | Burton et al. | 514/16 |
| 4,384,994 | 5/1983 | Veber et al. | 530/330 |
| 4,397,786 | 8/1983 | Evans et al. | 260/404 |
| 4,424,207 | 1/1984 | Szelke et al. | 514/15 |
| 4,485,099 | 11/1984 | Boger et al. | 514/11 |

FOREIGN PATENT DOCUMENTS

| | | |
|---|---|---|
| 0077029 | 7/1982 | European Pat. Off. |
| 0077028 | 7/1982 | European Pat. Off. |
| 1587809 | 3/1977 | United Kingdom . |

OTHER PUBLICATIONS

Umezawa et al., J. Antibiot., 23:259–262, 1970.
Tewksbury et al., Circulation, 59, 60, Supp. II: 132, 10/79.
Rich et al., J. Med. Chem., 23:27, 1980.
Skeggs, Jr. et al., J. Exp. Med., 106:439–453, 1957.
Kokubu et al., Biochem. Pharmacol., 22:3217–3223, 1973.
Burton et al., Biochemistry, 14:3892–3898, 1975.
Poulsen et al., Biochemistry, 12:3877–3882, 1973.
Szelke et al., Nature, 299, 555, 1982.
Szelke et al., Hypertension, 4, Supp. 2, 59, 1981.
Powers et al., Acid Proteases, Structure, Function and Biology, Plenum Press, 1977, 141–157.
Boger et al., Nature, 303:81–84, 1983.
Ondetti and Cushman, Biopolymers, 20:2001–2010, 1981.
Ondetti et al., Chemistry and Biology of Peptides, ed. J. Meienhofer, Ann Arbor Science, pp. 525–531, 1972.
Van Lommen et al., European Peptide Symposium 16th, Peptides, 1980, ed. K. Brunfeldt, Scriptor, Copenhagen, pp. 248–252, 1981.
Almquist et al., J. Med. Chem., 23:1392–1398, 1980.
Kawasaki and Maeda, Biochem. Biophys. Res. Commun., 106:113–116, 1982.
Fok and Yankellov, Biochem. Biophys. Res. Commun., 74:273–278, 1977.
Spatola and Bettag, J. Org. Chem., 45:2393–2394, 1981.
Hann et al., J. Chem. Soc. Chem. Commun., 234–235, 1980.
Cox et al., J. Chem. Soc. Chem. Commun., 799–800, 1980.
Atherton et al., J. Chem. Soc. (C)., 3393–3396, 1971.
Parry et al., Chemistry and Biology of Peptides, ed. J. Meienhofer, Ann Arbor Science, pp. 541–544, 1972.
Hudson et al., Int. J. Peptide Protein Res., 15:122–129, 1979.
Frank and Desiderio, Anal. Biochem., 90:413–419.
Marshall, Federation Proc., 35:2494–2501, 1976.
Burton et al., Proc. Natl. Acad. Sci. U.S.A., 77:5476–5479, 9/80.
Suketa et al., Biochemistry, 14:3188, 1975.
Swales, Pharmac. Ther., 7:173–201, 1979.
Kokubu et al., Nature, 217:456–457, 2/3/68.
Matsushita et al., J. Antibiotics, 28:1016–1018, 12/75.
Lazar et al., Biochem. Pharma., 23:2776–2778, 1974.
Miller et al., Biochem. Pharma., 21:2941–2944, 1972.
Haber, Clinical Science, 59:7s–19s, 1980.

*Primary Examiner*—Delbert R. Phillips
*Attorney, Agent, or Firm*—Richard A. Elder; Hesna J. Pfeiffer

[57] ABSTRACT

Cyclic renin-inhibitory peptides of the formula

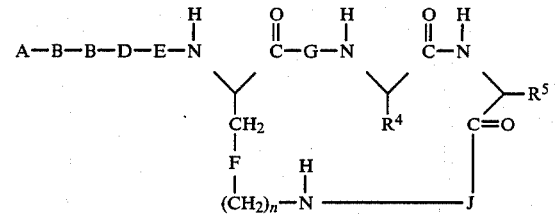

wherein G is an isostere component substituted into the substrate analogy at the cite of the enzyme cleavage, and analogs thereof, which inhibit renin and are useful for treating various forms of renin-associated hypertension and hyperaldosteronism.

9 Claims, No Drawings

C-TERMINAL AMIDE CYCLIC RENIN INHIBITORS CONTAINING PEPTIDE ISOSTERES

BACKGROUND OF THE INVENTION

1. Field of The Invention

The present invention is concerned with novel peptides which inhibit renin.

The present invention is also concerned with pharmaceutical compositions containing the novel peptides of the present invention as active ingredients, with methods of treating renin-associated hypertension and hyperaldosteronism, with diagnostic methods which utilize the novel peptides of the present invention, and with methods of preparing the novel peptides of the present invention.

Renin is a proteolytic enzyme of molecular weight about 40,000, produced and secreted by the kidney. It is secreted by the juxtaglomerular cells and acts on the plasma substrate, angiotensinogen, to split off the decapeptide angiotensin I, which is converted to the potent pressor agent angiotensin II. Thus, the renin-angiotensin system plays an important role in normal cardiovascular homeostasis and in some forms of hypertension.

In the past, attempts to modulate or manipulate the renin-angiotensin system have met with success in the use of inhibitors of angiotensin I converting enzyme. In view of this success, it seems reasonable to conclude that a specific inhibitor of the limiting enzymatic step that ultimately regulates angiotensin II production, the action of renin on its substrate, would be at least equally successful. Thus, an effective inhibitor of renin has been long sought as both a therapeutic agent and as an investigative tool.

2. Brief Description of the Prior Art

There has been substantial interest in the synthesis of useful renin inhibitors for many decades; and the following table lists the major classes of renin inhibitors that have been studied, as well as their inhibition constants ($K_i$):

| Class | $K_i$ (M) |
| --- | --- |
| Renin antibody | probably $10^{-6}$ |
| Pepstatin | $10^{-6}$–$10^{-7}$ |
| Phospholipids | $10^{-3}$ |
| Substrate analogs | |
| Tetrapeptides | $10^{-3}$ |
| Octa- to tridecapeptides | $10^{-5}$–$10^{-6}$ |

Umezawa et al., in *J. Antibiot. (Tokyo)* 23: 259–262, 1970, reported the isolation of a peptide from actinomyces that was an inhibitor of aspartyl proteases such as pepsin, cathepsin D, and renin. This peptide, known as pepstatin, was found by Gross et al., *Science* 175: 656, 1971, to reduce blood pressure in vivo after the injection of hog renin into nephrectomized rats. However, pepstatin has not found wide application as an experimental agent because of its limited solubility and its inhibition of a variety of other acid proteases in addition to renin. The structure of pepstatin is shown below:

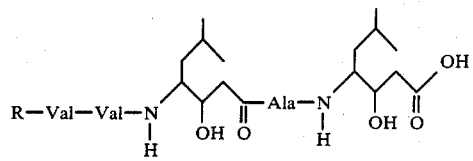

To date, many efforts have been made to prepare a specific renin inhibitor based on substrate analogy. Since the human renin substrate has only recently been elucidated (Tewksbury et al., *Circulation* 59, 60, Supp. II: 132, Oct. 1979), heretofore substrate analogy has been based on the known pig renin substrate. While the human and pig renin substrates are not the same, the substrate analogy based on pig renin has always been considered acceptable in the art as predictive of human renin inhibitory activity because of the closely related activity of the two renins. Thus, while pig renin does not cleave the human renin substrate, human renin, on the other hand, does cleave the pig renin substrate. See Poulsen et al., *Biochim. Biophys. Acta* 452: 533–537, 1976; and Skeggs, Jr. et al., *J. Exp. Med.* 106: 439–453, 1957. Moreover, the human renin inhibitory activity of the peptides of the present invention most active in inhibiting pig renin has been confirmed, thus providing further evidence of this accepted correlation between human and pig renin activity.

It has been found, for example, using pig renin substrate analogy, that the octapeptide sequence extending from histidine-6 throough tyrosine-13 has kinetic parameters essentially the same as those of the full tetradecapeptide renin substrate. The amino acid sequence of the octapeptide in pig renin substrate is as follows:

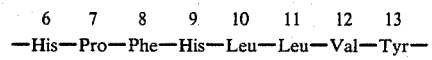

Renin cleaves this substrate between Leu[10] and Leu[11].

Kokubu et al., *Biochem. Pharmacol.* 22: 3217–3223, 1973, synthesized a number of analogs of the tetrapeptide found between residues 10 to 13, but while inhibition could be shown, inhibitory constants were only of the order of $10^{-3}$M.

Analogs of a larger segment of renin substrate were also synthesized: Burton et al., *Biochemistry* 14: 3892–3898, 1975, and Poulsen et al., *Biochemistry* 12: 3877–3882, 1973. Two of the major obstacles which had to be overcome to obtain an effective renin inhibitor useful in vivo were lack of solubility and weak binding (large inhibitory constant). Modifications to increase solubility soon established that the inhibitory properties of the peptides are markedly dependent on the hydrophobicity of various amino acid residues, and that increasing solubility by replacing lipophilic amino acids with hydrophilic isosteric residues becomes counterproductive. Other approaches to increasing solubility have had limited success. Various modifications designed to increase binding to renin have also been made, but here too, with only limited success. For a more detailed description of past efforts to prepare an effective inhibitor of renin, see Haber and Burton, *Fed. Proc. Fed. Am. Soc. Exp. Biol.* 38: 2768–2773, 1979.

More recently, Szelke et al., in work described in European Patent Publication No. 45,665; *Nature*, 229, 555 (1982); *Hypertension*, 4, Supp. 2, 59, 1981; British Pat. No. 1,587,809; and "Novel Transition-State Analogue Inhibitors of Renin", a presentation at the Eighth American Peptide Symposium, May 22-27, 1983, Tucson, Ariz., have replaced the Leu-Leu site of renin cleavage by isosteric substitution, and obtained compounds with excellent potency.

Powers et al., in *Acid Proteases, Structure, Function and Biology*, Plenum Press, 1977, 141-157 have suggested that in pepstatin, statine occupies the space of the two amino acids on either side of the cleavage site of a pepsin substrate, and Tang et al., in *Trends in Biochem. Sci.*, 1: 205-208 (1976) and *J. Biol. Chem.*, 251: 7088-94, 1976, have proposed that the statine residue of pepstatin resembles the transition state for pepsin hydrolysis of peptide bonds. However, the applicability of these concepts to renin inhibitors is not taught in any of these references, and would be speculative due to the known high degree of specificity of the renin enzyme.

Veber and Rich, in U.S. Pat. No. 4,384,994 and published European patent application No. 0,007,029; Evans and Rittle, in U.S. Pat. No. 4,397,786; Veber and Boger, in published European patent application No. 0,077,028; Boger at al., *Nature*, 303: 81-84 (1983); have all described renin inhibitory peptides containing statine. However, none of these references describe or suggest the present invention.

Preparation and use of peptide isosteres of the type employed in the present invention is described in the following references, which do not, however, disclose or suggest the renin inhibitors of the present invention: Natarajan et al., *Peptides Synthesis—Structure—Function*, ed. D. H. Rich and E. Gross, Pierce Chem. Co., Rockford, Ill., pp. 429-433, 1981; Ondetti and Cushman, *Biopolymers*, 20: 2001-2010, 1981; Ondetti et al., *Chemistry and Biology of Peptides*, ed. J. Meienhofer, Ann Arbor Science, pp. 525-531, 1972; Van Lommen et al., European Peptide Symposium 16th, *Peptides 1980*, ed. K. Brunfeldt, Scriptor, Copenhagen, pp. 248-252, 1981; Almquist et al., *J. Med. Chem.* 23: 1392-1398, 1980; Kawasaki and Maeda, *Biochem. Biophys. Res. Commun.* 106: 113-116, 1982; Fok and Yankellov, *Biochem. Biophys. Res. Commun.* 74: 273-278, 1977; Spatola et al., *Peptides. Structure—Function—Biological Function*, ed. E. Gross and J. Meienhofer, Pierce Chem. Col, Rockford, Ill., pp. 273-276, 1979; Spatola and Bettag, *J. Org. Chem.* 46: 2393-2394, 1981; Hann et al., *J. Chem. Soc. Chem. Commun.*, 234-235, 1980; Cox et al., *J. Chem. Soc. Chem. Commun.*, 799-800, 1980; Atherton et al., *J. Chem. Soc. (C)*, 3393-3396, 1971; Parry et al., *Chemistry and Biology of Peptides*, ed. J. Meienhofer, Ann Arbor Science, pp. 541-544, 1972; Hudson et al., *Int. J. Peptide Protein Res.* 15: 122-129, 1979; and Frank and Desiderio, *Anal. Biochem.* 90: 413-419.

For other articles describing previous efforts to devise renin inhibitors, see Marshall, *Federation Proc.* 35: 2492-2501, 1976; Burton et al., *Proc. Natl. Acad. Sci. USA* 77: 5476-5479, Sept. 1980; Suketa et al., *Biochemistry* 14: 3188, 1975; Swales, *Pharmac. Ther.* 7: 173-201, 1979; Kokubu et al., *Nature* 217: 456-457, Feb. 3, 1968; Matsushita et al., *J. Antibiotics* 28: 1016-1018, Dec. 1975; Lazar et al., *Biochem. Pharma.* 23: 2776-2778, 1974; Miller et al., *Biochem. Pharma.* 21: 2941-2944, 1972; Haber, *Clinical Science* 59: 7s-19s, 1980; Rich et al., *J. Org. Chem.* 42: 3624, 1978, and *J. Med. Chem.* 23: 27, 1980; Burton et al., U.S. Pat. No. 4,269,827; Castro et al., U.S. Pat. No. 4,185,096; and Sankyo Japan Pat. No. 76-067001.

DESCRIPTION OF THE INVENTION

The present invention relates to renin-inhibitory cyclic peptides of the formula:

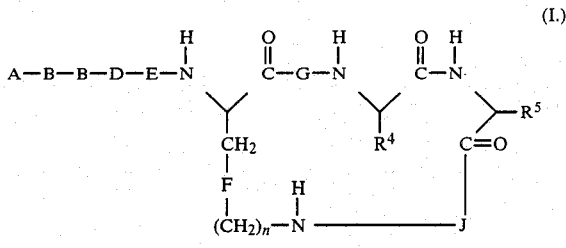

(I.)

wherein:
A is hydrogen; or

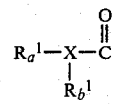

where
X is

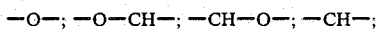

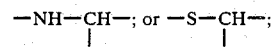

and
$R_a^1$ and $R_b^1$ may be the same or different and are hydrogen; $W\!-\!(CH_2)_p\!-\!$ or $W\!-\!(CH_2)_p$, $-CH\!=\!CH\!-\!(CH_2)_{p''}$, where W is $C_{1-4}$alkyl; hydrogen; aryl; $C_{3-7}$cycloalkyl; or $C_{3-7}$cycloalkyl or aryl substituted with up to five members independently selected from the group consisting of $C_{1-8}$alkyl, trifluoromethyl, hydroxy, $C_{1-4}$alkoxy, and halo; p is 0 to 5; and p' and p'' are independently 0 to 2; except that where X is $-\!O\!-\!$, only one of $R_a^1$ or $R_b^1$ is present;

B is absent; glycyl; sarcosyl; or

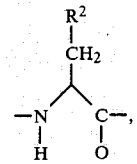

where $R^2$ is hydrogen; $C_{1-4}$alkyl; hydroxy $C_{1-4}$alkyl; aryl; aryl substituted with up to three members selected from the group consisting of $C_{1-4}$alkyl, trifluoromethyl, hydroxy, $C_{1-4}$alkoxy, and halo; indolyl; 4-imidazolyl; amino $C_{2-4}$alkyl; acyl $C_{2-4}$alkyl where the acyl is

and $R^8$ is hydrogen, $C_{1-4}$alkyl, hydroxy, or $C_{3-7}$cycloalkyl; guanidyl $C_{2-3}$alkyl; or methylthiomethyl;
D is absent; or

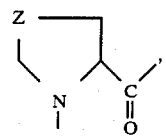

where Z is —(CH$_2$)$_m$— and m is 1 or 2; or —S—;
E is absent; or

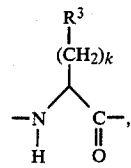

where k is 1 to 4; and R$^3$ is hydrogen; C$_{1-4}$alkyl; aryl; aryl C$_{1-4}$alkyl; aryl C$_{1-4}$alkyl or aryl where the aryl portion is substituted with up to three members selected from the group consisting of C$_{1-4}$alkyl, trifluoromethyl, hydroxy, C$_{1-4}$alkoxy, and halo; or indolyl;
F is absent; —CH$_2$—; —S—; or —O—;
n is 0 to 3;
G is

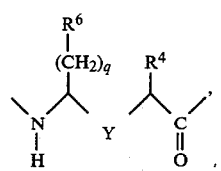

where
R$^6$ is C$_{3-6}$alkyl; C$_{3-7}$cycloalkyl; aryl; or C$_{3-7}$cycloalkyl or aryl substituted with up to three members selected from the group consisting of C$_{1-4}$alkyl, trifluoromethyl, hydroxy, C$_{1-4}$alkoxy, and halo;
q is 1 to 4;
R$^4$ is as defined below; and
Y is

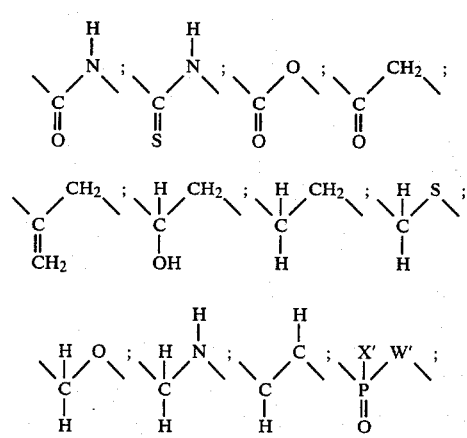

wherein X' is hydroxy; amino; or mono- or di-C$_{1-4}$alkyl amino; and W' is absent; —O—; —NH—; or —CH$_2$—;

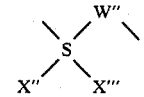

where X" and X"' are independently absent; or

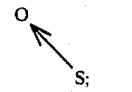

and W" is absent; —CH$_2$—; or

where R8 is hydrogen or C$_{1-3}$alkyl;

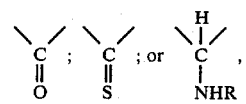

wherein R is hydrogen; C$_{1-4}$alkyl; formyl; C$_{1-4}$alkanoyl; aroyl; carboxy; C$_{1-4}$alkoxycarbonyl; aryloxycarbonyl; or aryl C$_{1-4}$alkoxycarbonyl;
R$^4$ is hydrogen; or

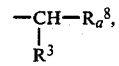

where R$^3$ is hydrogen; C$_{1-4}$alkyl; aryl; aryl C$_{1-4}$alkyl; or aryl C$_{1-4}$alkyl or aryl where the aryl portion is substituted with up to three members selected from the group consisting of C$_{1-4}$alkyl, trifluoromethyl, hydroxy, C$_{1-4}$alkoxy, and halo; or indolyl; and R$_a$$^8$ is hydrogen; C$_{1-4}$alkyl; hydroxy; or C$_{3-7}$cycloalkyl;
R$^5$ is hydrogen;

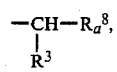

where R$^3$ and R$_a$$^8$ are as defined above; or —(CH$_2$)$_{n'}$—R$^9$, where n' is 0 or 1-4; and R$^9$ is heterocyclic; heterocyclic substituted with up to five members independently selected from the group consisting of C$_{1-6}$alkyl, hydroxy, trifluoromethyl, C$_{1-4}$alkoxy, halo, aryl, aryl C$_{1-4}$alkyl, amino, and mono- or di-C$_{1-4}$alkylamino; guanidyl C$_{2-3}$alkyl; or amino C$_{1-4}$alkyl;
J is absent; or glycyl; and
wherein all of the asymmetric carbon atoms have an S configuration, except for those in the B, D and Y portion of G substituents, which may have an S or R configuration; and pharmaceutically-acceptable salts thereof.

While both the S and R chiralities for asymmetric carbon atoms in the B, D and Y portion of G substituents are included in the peptides of the present invention, preferred chiralities are indicated in the description which follows.

In the above definitions, the term "alkyl" is intended to include both branched and straight chain hydrocarbon groups having the indicated number of carbon atoms.

The term "halo" means fluoro, chloro, bromo and iodo.

The aryl substituent represents phenyl, and naphthyl.

The heterocyclic substituent recited above represents any 5- or 6-membered ring containing from one to three heteroatoms selected from the group consisting of nitrogen, oxygen, and sulfur; having various degrees of unsaturation; wherein the nitrogen and sulfur heteroatoms may optionally be oxidized; wherein the nitrogen heteroatom may optionally be quaternized; and including any bicyclic group in which any of the above heterocyclic rings is fused to a benzene ring. Heterocyclic substituents in which nitrogen is the heteroatom are preferred, and of these, those containing a single nitrogen atom are preferred. Fully saturated heterocyclic substituents are also preferred. Thus, piperidine is a preferred heterocyclic substituent. Other preferred heterocyclic substituents are: pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

Where the heterocyclic substituent itself is substituted, it is preferred that the substituent is aryl$C_{1-4}$alkyl.

The novel renin inhibitory peptides of the present invention may also be described in terms of common amino acid components and closely related analogs thereof, in accordance with the following formula:

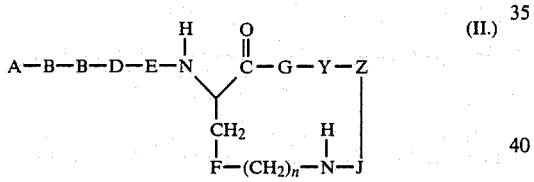

The A, B, D, E, F, G and J components correspond to the same portions of Formula I.

The common amino acid components of Formula II are as follows:

A has the same meaning as above in Formula I;
B is Ala, Leu, Ser, Thr, Phe, Tyr, Trp, His, Lys, Orn, Arg, or Met;
D is Pro;
E is Ala, Leu, Phe, HomoPhe, BisHomoPhe, Tyr, HomoTyr, Trp, or HomoTrp;
F has the same meaning as above in Formula I;
G has the same meaning as above in Formula I;
Y is Gly, Ala, Val, Leu, Ile, Ser, Thr, Phe, Tyr, or Trp;
Z is the same as Y and may also be Lys, Orn, Arg, or His; and
J is Gly and one end of the cyclical structure, or, when absent, Z is that end.

It will be understood that closely related analogs of the above common amino acids, for example, aliphatic amino acids in addition to Ala, Val, Leu, and Ile, such as α-aminobutyric acid (Abu), and substituted phenyl derivatives of Phe, are included in the broad description of the novel inhibitory peptides of the present invention represented by Formula I and its definitions. Thus, the peptides of Formula II and its definitions represent preferred peptides of the present invention.

Preferred inhibitory peptides of the present invention are the following:

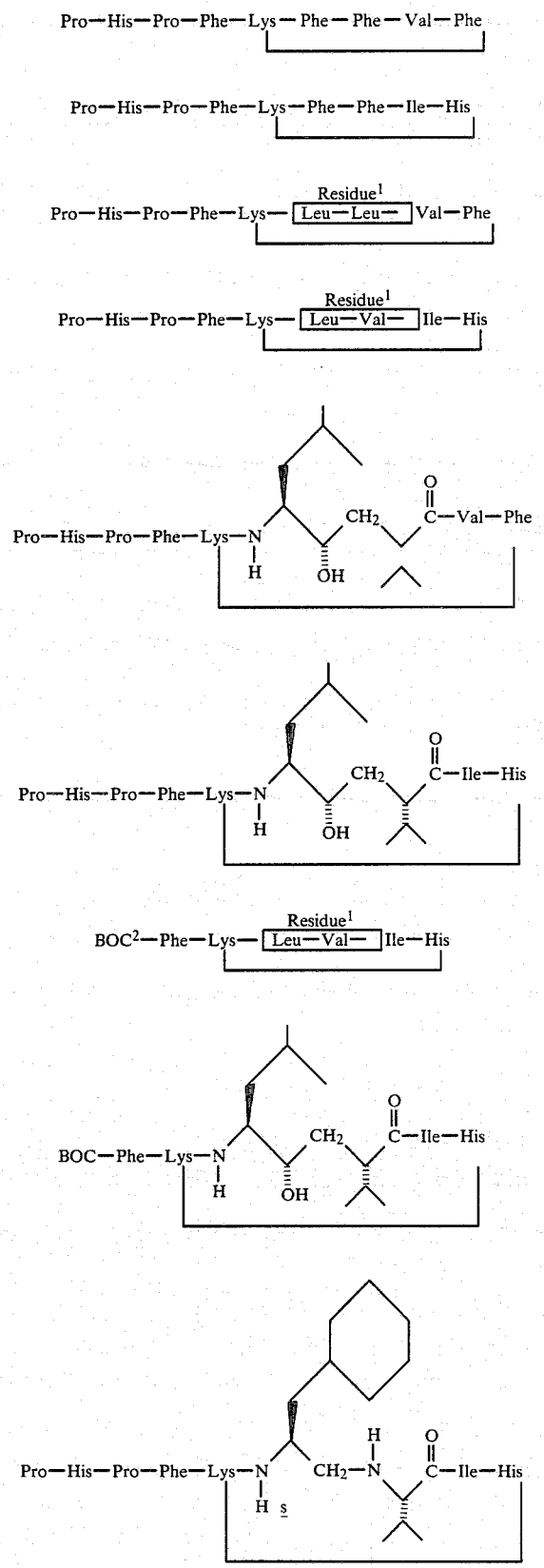

-continued

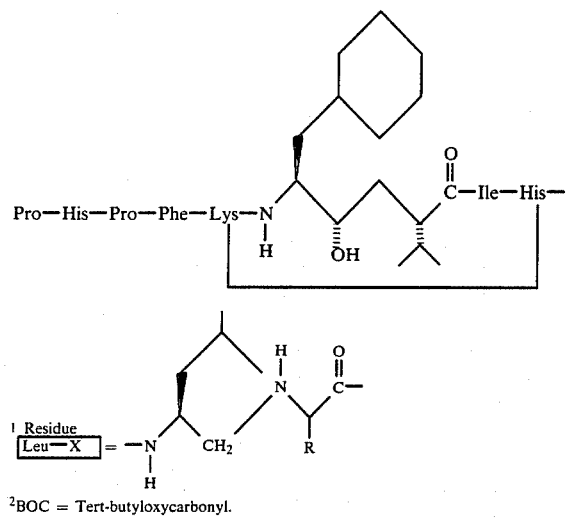

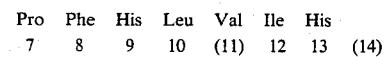
[2]BOC = Tert-butyloxycarbonyl.

The inhibitory peptides of the present invention may be better appreciated in terms of substrate analogy from the following illustration of Formula I alongside the octapeptide sequence of a portion of the pig renin substrate, which renin cleaves between Leu[10] and Leu[11]:

| Pro | Phe | His | Leu | Leu | Val | Tyr | |
|---|---|---|---|---|---|---|---|
| 7 | 8 | 9 | 10 | (11) | 12 | 13 | (14) |

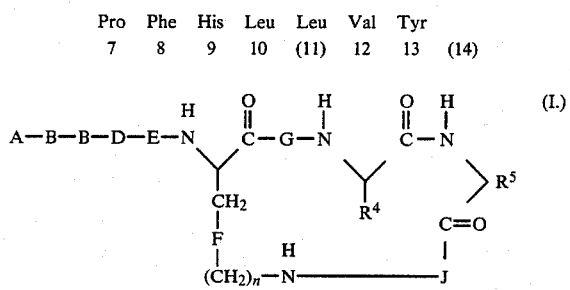

As can be seen, a unique aspect and essential feature of the present invention is the substitution of a peptide isostere component for the double amino acid sequence: Leu[10]-Leu[11] in the endogenous pig renin substrate. It is believed that substitution of this isostere component for both leucine amino acids rather than just one leucine results in an improved substrate analogy due to the greater linear extent of the isostere component as compared to a single leucine component. Thus, the isostere component more closely approximates Leu-Leu in linear extent, and thereby provides a better "fit" to the renin enzyme.

The inhibitory peptides of the present invention may also be better appreciated in terms of substrate analogy from the following illustration of Formula I alongside the octapeptide sequence of a portion of the human renin substrate, which renin cleaves between Leu[10] and Val[11]:

| Pro | Phe | His | Leu | Val | Ile | His | |
|---|---|---|---|---|---|---|---|
| 7 | 8 | 9 | 10 | (11) | 12 | 13 | (14) |

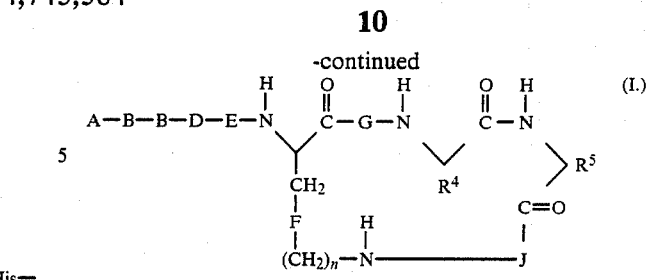

As can be seen, a unique aspect and essential feature of the present invention is the substitution of a peptide isostere component for the double amino acid sequence: Leu[10]-Val[11] in the endogenous human renin substrate. It is believed that substitution of this isostere component for both the leucine and valine amino acids rather than just the leucine results in an improved substrate analogy due to the greater linear extent of the isostere component as compared to a single leucine component. Thus, the isostere component more closely approximates Leu-Val in linear extent, and thereby provides a better "fit" to the human renin enzyme.

In the endogenous substrate it is also preferred to substitute Leu for Val[12] and Phe for Tyr[13] in order to enhance the inhibitory activity of the resulting peptide.

The Formula I compounds can be used in the form of salts derived from inorganic or organic acids and bases. Included among such acid addition salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The present invention is also directed to combinations of the novel renin-inhibitory peptides of Formula I with one or more antihypertensive agents selected from the group consisting of diuretics, α and/or β-adrenergic blocking agents, CNS-acting agents, adrenergic neuron blocking agents, vasodilators, angiotensin I converting enzyme inhibitors, and other antihypertensive agents.

For example, the compounds of this invention can be given in combination with such compounds or salt or other derivative forms thereof as:

Diuretics: acetazolamide; amiloride; bendroflumethiazide; benzthiazide; bumetanide; chlorothiazide; chlorthalidone; cyclothiazide; ethacrynic acid; furosemide; hydrochlorothiazide; hydroflumethiazide; indacrinone (racemic mixture, or as either the (+) or (−) enantiomer alone, or a manipulated ratio, e.g., 9:1 of said enantiomers, respectively); metolazone; methyclothiazide; muzolimine; polythiazide; quinethazone; sodium ethacrynate; sodium nitroprusside; spironolactone; ticrynafen; triamterene; trichlormethiazide;

α-Adrenergic Blocking Agents: dibenamine; phentolamine; phenoxybenzamine; prazosin; tolazoline;

β-Adrenergic Blocking Agents: atenolol; metoprolol; nadolol; propranolol; timolol;

((±)-2-[3-(tert-butylamino)-2-hydroxypropoxy]-2-furananilide) (ancarolol);

(2-acetyl-7-(2-hydroxy-3-isopropylaminopropoxy)benzofuran HCl) (befunolol);

((±)-1-(isopropylamino)-3-(p-(2-cyclopropylmethoxyethyl)-phenoxy)-2-propanol HCl) (betaxolol);

(1-[(3,4-dimethoxyphenethyl)amino]-3-(m-tolyloxy)-2-propanol HCl) (bevantolol);

(((±)-1-(4-((2-isopropoxyethoxy)methyl)phenoxy)-3-isopropylamino-2-propanol)fumarate) bisoprolol);

(4-(2-hydroxy-3-[4-(phenoxymethyl)-piperidino]-propoxy)-indole);

(carbazolyl-4-oxy-5,2-(2-methoxyphenoxy)-ethylamino-2-propanol);

(1-((1,1-dimethylethyl)amino)-3-((2-methyl-1H-indol-4-yl)oxy)-2-propanol benzoate) (bopindolol);

(1-(2-exobicyclo[2.2.1]-hept-2-ylphenoxy)-3-[(1-methylethyl)-amino]-2-propanol HCl) (bornaprolol);

(o-[2-hydroxy-3-[(2-indol-3-yl-1,1-dimethylethyl)amino]propoxy]benzonitrile HCl) (bucindolol);

(α-[(tert.butylamino)methyl]methyl]-7-ethyl-2-benzofuranmethanol) (bufuralol);

(3-[3-acetyl-4-[3-(tert.butylamino)-2-hydroxypropyl]-phenyl]-1,1-diethylurea HCl) (celiprolol);

((±)-2-[2-[3-[(1,1-dimethylethyl)amino]-2-hydroxypropoxy]phenoxy]-N-methylacetamide HCl) (cetamolol)

(2-benzimidazolyl-phenyl(2-isopropylaminopropanol));

((±)-3′-acetyl-4′-(2-hydroxy-3-isopropylaminopropoxy)acetanilide HCl) (diacetolol);

(methyl-4-[2-hydroxy-3-[(1-methylethyl)aminopropoxy]]-benzenepropanoate HCl) (esmolol);

(erythro-DL-1-(7-methylindan-4-yloxy)-3-isopropylaminobutan-2-ol);

(1-(tert.butylamino)-3-[O-(2-propynyloxy)phenoxy]-2-propanol (pargolol);

(1-(tert.butylamino)-3-[o-(6-hydrazino-3-pyridazinyl)-phenoxy]-2-propanol diHCl) (prizidilol);

((−)-2-hydroxy-5-[(R)-1-hydroxy-2-[(R)-(1-methyl-3-phenylpropyl)amino]ethyl]benzamide);

(4-hydroxy-9-[2-hydroxy-3-(isopropylamino)-propoxy]-7-methyl-5H-furo[3,2-g][1]-benzopyran-5-one) (iprocrolol);

((−)-[5-(tert.butylamino)-2-hydroxypropoxy]-3,4-dihydro-1-(2H)-naphthalenone HCl) (levobunolol);

(4-(2-hydroxy-3-isopropylamino-propoxy)-1,2-benzisothiazole HCl);

(4-[3-(tert.butylamino)-2-hydroxypropoxy]-N-methylisocarbostyril HCl);

((±)-N-2-[4-(2-hydroxy-3-isopropyl aminopropoxy)-phenyl]ethyl-N′-isopropylurea) (pafenolol);

(3-[[(2-trifluoroacetamido)ethyl]amino]-1-phenoxypropan-2-ol);

(N-(3-(o-chlorophenoxy)-2-hydroxypropyl)-N′-(4′-chloro-2,3-dihydro-3-oxo-5-pyridazinyl)ethylenediamine);

((±)-N-[3-acetyl-4-[2-hydroxy-3-[(1methylethyl)amino]propoxy]phenyl]butanamide) (acebutolol);

((±)-4′-[3-(tert.butylamino)-2-hydroxypropoxy]spiro[cyclohexane-1,2′-indan]-1′-one) (spirendolol);

(7-[3-[[2-hydroxy-3-[(2-methylindol-4-yl)oxy]propyl]amino]butyl]thiophylline) (teoprolol);

((±)-1-tert.butylamino-3-(thiochroman-8-yloxy)-2-propanol) (tertatolol);

((±)-1-tert.butylamino-3-(2,3-xylyloxy)-2-propanolHCl) (xibenolol);

(8-[3-(tert.butylamino)-2-hydroxypropoxy]-5-methylcoumarin) (bucumolol);

(2-(3-(tert.butylamino)-2-hydroxy-propoxy)benzonitrile HCl) (bunitrolol);

((±)-2′-[3-(tert-butylamino)-2-hydroxypropoxy]-5′-fluorobutyrophenone) (butofilolol);

(1-(carbazol-4-yloxy)-3-(isopropylamino)-2-propanol) (carazolol);

(5-(3-tert.butylamino-2-hydroxy)propoxy-3,4-dihydrocarbostyril HCl) (carteolol);

(1-(tert.butylamino)-3-(2,5-dichlorophenoxy)-2-propanol) (cloranolol);

(1-(inden-4(or 7)-yloxy)-3-(isopropylamino)-2-propanol HCl) (indenolol);

(1-isopropylamino-3-[(2-methylindol-4-yl)oxy]-2-propanol) (mepindolol);

(1-(4-acetoxy-2,3,5-trimethylphenoxy)-3-isopropylaminopropan-2-ol) (metipranolol);

(1-(isopropylamino)-3-(o-methoxyphenoxy)-3-[(1-methylethyl)amino]-2-propanol) (moprolol);

((1-tert.butylamino)-3-[(5,6,7,8-tetrahydro-cis-6,7-dihydroxy-1-naphthyl)oxy]-2-propanol) (nadolol);

((S)-1-(2-cyclopentylphenoxy)-3-[(1,1-dimethylethyl)amino]-2-propanol sulfate (2:1)) (penbutolol);

(4′-[1-hydroxy-2-(amino)ethyl]methanesulfonanilide) (sotalol);

(2-methyl-3-[4-(2-hydroxy-3-tert.butylaminopropoxy)-phenyl]-7-methoxy-isoquinolin-1-(2H)-one);

(1-(4-(2-(4-fluorophenyloxy)ethoxy)phenoxy)-3-isopropylamino-2-propanol HCl);

((−)-p-[3-[(3,4-dimethoxyphenethyl)amino]-2-hydroxypropoxy]-β-methylcinnamonitrile) (pacrinolol);

((±)-2-(3′-tert.butylamino-2′-hydroxypropylthio)-4-(5′-carbamoyl-2′-thienyl)thiazole (HCl) (arotinolol);

((±)-1-[p-[2-(cyclopropylmethoxy)ethoxy]phenoxy]-3-(isopropylamino)-2-propanol) (cicloprolol);

((±)-1-[(3-chloro-2-methylindol-4-yl)oxy]-3-[(2-phenoxyethyl)amino]-2-propanol) (indopanolol);

((±)-6-[[2-[[3-(p-butoxyphenoxy)-2-hydroxypropyl]amino]ethyl]amino]-1,3-dimethyluracil) (pirepolol);

(4-(cyclohexylamino)-1-(1-naphtholenyloxy)-2-butanol);

(1-phenyl-3-[2-[3-(2-cyanophenoxy)-2-hydroxypropyl]-aminoethyl]hydantoin HCL);

(3,4-dihydro-8-(2-hydroxy-3-isopropylaminopropoxy)-3-nitroxy-2H-1-benzopyran) (nipradolol);

α and β-Adrenergic Blocking Agents:

((±)-1-tert.butylamino-3-[o-[2-(3-methyl-5-isoxazolyl)vinyl]phenoxy]-2propanol) (isoxoprolol);

(1-isopropylamino-3-(4-(2-nitroxyethoxy)phenoxy)-2-propanol HCl);

(4-hydroxy-α-[[3-(4-methoxyphenyl)-1-methylpropyl]aminomethyl]-3-(methylsulfinyl)-benzmethanol HCl) (sulfinalol);

(5-[1-hydroxy-2-[[2-(o-methoxyphenoxy)ethyl]amino]ethyl]-2-methylbenzenesulfonamide HCl);

(5-[1-hydroxy-2-[(1-methyl-3-phenylpropyl)amino]ethyl]salicylamide HCl) (labetalol);

(1-((3-chloro-2-methyl-1H-indol-4-yl)oxy)-3-((2-phenoxyethyl)amino)-2-propanol-hydrogenmalonate) (ifendolol);
(4-(2-hydroxy-3-[(1-methyl-3-phenylpropyl)amino]-propoxy)benzeneacetamide);
(1-[3-[[3-(1-naphthoxy)-2-hydroxypropyl]-amino]-3,3-dimethyl-propyl]-2-benzimidazolinone);
(3-(1-(2-hydroxy-2-(4-chlorophenylethyl))-4-piperidyl)-3,4-dihydroxy)quinoxolin-2(1H)-one);
CNS-Acting Agents: clonidine; methyldopa;
Adrenergic Neuron Blocking Agents: guanethidine; reserpine and other rauwolfia alkaloids such as rescinnamine;
Vasodilators: diazoxide; hydralazine; minoxidil;
Angiotensin I Converting Enzyme Inhibitors:
1-(3-mercapto-2-2-methyl-1-oxopropyl)-L-proline (captopril);
(1-(4-ethoxycarbonyl-2,4(R,R)-dimethylbutanol)indoline-2(S)-carboxylic acid);
(2-[2-[[1-(ethoxycarbonyl)-3-phenyl-propyl]amino]-1-oxopropyl]-1,2,3,4-tetrahydro-3-isoquinoline carboxylic acid);
((S)-1-[2-[[1-(ethoxycarbonyl)-3-phenylpropyl]amino]-1-oxopropyl]octahydro-1H-indole-2-carboxylic acid HCl);
(N-cyclopentyl-N-(3-(2,2-dimethyl-1-oxopropyl)thiol-2-methyl-1-oxopropyl)glycine) (pivalopril);
((2R,4R)-2-(2-hydroxyphenyl)-3-(3-mercaptopropionyl)-4-thiazolidinecarboxylic acid;
(1-(N-[1(S)-ethoxycarbonyl-3-phenylpropyl]-(S)-alanyl)cis,syn-octahydroindol-2(S)-carboxylic acid HCl);
((−)-(S)-1-[(S)-3-mercapto-2-methyl-1-oxopropyl]indoline-2-carboxylic acid);
([1(S),4S]-1-[3-(benzoylthio)-2-methyl-1-oxopropyl]-4-phenylthio-L-proline;
(3-([1-ethoxycarbonyl-3-phenyl-(1S)-propyl]amino)-2,3,4,5-tetrahydro-2-oxo-1-(3S)-benzazepine-1-acetic acid HCl);
(N-(2-benzyl-3-mercaptopropanoyl)-S-ethyl-L-cysteine) and the S-methyl analogue;
(N-(1(S)-ethoxycarbonyl-3-phenylpropyl)-L-alanyl-L-proline maleate) (enalapril);
N-[1-(S)-carboxy-3-phenylpropyl]-L-alanyl-1-proline;
$N^2$-[1-(S)-carboxy-3-phenylpropyl]-L-lysyl-L-proline (lysinopril);
Other Antihypertensive Agents: aminophylline; cryptenamine acetates and tannates; deserpidine; meremethoxylline procaine; pargyline; trimethaphan camsylate; and the like, as well as admixtures and combinations thereof.

Typically, the individual daily dosages for these combinations can range from about one-fifth of the minimally recommended clinical dosages to the maximum recommended levels for the entities when they are given singly. Coadministration is most readily accomplished by combining the active ingredients into a suitable unit dosage form containing the proper dosages of each. Other methods of coadministration are, of course, possible.

The novel peptides of the present invention possess an excellent degree of activtiy in treating renin-associated hypertension and hyperaldosteronism.

For these purposes the compounds of the present invention may be administered parenterally, by inhalation spray, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions may be in the form of a sterile injectable preparation, for example as a sterile injectable aqueous or oleagenous suspension. This suspension may be formulated according to the known art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The peptides of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order of 0.1 to 4.0 grams per day are useful in the treatment of the above indicated conditions. For example, renin-associated hypertension and hyperaldosteronism are effectively treated by the administration of from 1.0 to 50 milligrams of the compound per kilogram of body weight per day.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Thus, in accordance with the present invention there is further provided a pharmaceutical composition for treating renin-associated hypertension and hyperaldosteronism, comprising a pharmaceutical carrier and a therapeutically effective amount of a peptide of the formula:

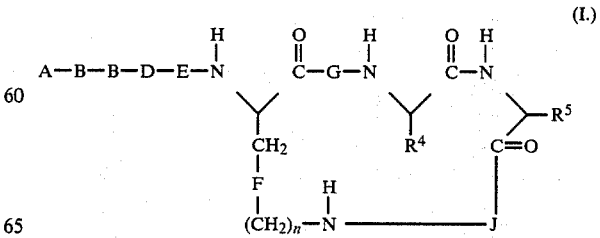

wherein A, B, D, E, F, G, J, $R^4$ and $R^5$ have the same meaning as recited further above for Formula I;

wherein all of the asymmetric carbon atoms have an S configuration, except for those in the B, D, and Y portion of the G substituents, which may have an S or R configuration; and a pharmaceutically acceptable salt thereof.

Also, in accordance with the present invention there is still further provided a method of treating renin-associated hypertension and hyperaldosteronism, comprising administering to a patient in need of such treatment, a therapeutically effective amount of a peptide of the formula:

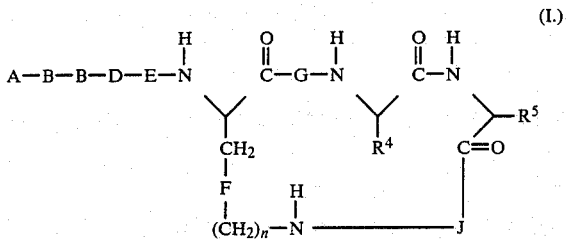

wherein A, B, D, E, F, G, H, $R^4$ and $R^5$ have the same meaning as recited further above for Formula I; wherein all of the asymmetric carbon atoms have an S configuration, except for those in the B, D, and Y portion of G substituents, which may have an S or R configuration; and a pharmaceutically acceptable salt thereof.

The renin inhibitory novel peptides of the present invention may also be utilized in diagnostic methods for the purpose of establishing the significance of renin as a causative or contributory factor in hypertension or hyperaldosteronism in a particular patient. For this purpose the novel peptides of the present invention may be administered in a single dose of from 0.1 to 10 mg per kg of body weight.

Both in vivo and in vitro methods may be employed. In the in vivo method, a novel peptide of the present invention is administered to a patient, preferably by intravenous injection, although parenteral administration is also suitable, at a hypotensive dosage level and as a single dose, and there may result a transitory fall in blood pressure. This fall in blood pressure, if it occurs, indicates supranormal plasma resin levels.

An in vitro method which may be employed involves incubating a body fluid, preferably plasma, with a novel peptide of the present invention and, after deproteinization, measuring the amount of angiotensin II produced in nephrectomized, pentolinium-treated rats. Another in vitro method involves mixing the plasma or other body fluid with a novel peptide of the present invention and injecting the mixture into a test animal. The difference in pressor response with and without added peptide is a measure of the resin content of the plasma.

Pepstatin may be employed in the methods described above as an active control. See, e.g., U.S. Pat. Nos. 3,784,686 and 3,873,681 for a description of the use of pepstatin in diagnostic methods of this type.

The novel peptides of the present invention may be prepared in accordance with well-known procedures for preparing peptides from their constituent amino acids, which will be described in more detail below.

A general method of preparation may be described in the following terms; wherein amino acids forming peptides of various lengths are sequentially assigned a Roman numeral for each peptide, rather than on the basis of a position on the overall peptide Formula I:

A method of preparing a peptide of Formula I, said peptide being comprised of from three to eight amino acids identified as I through VIII, amino acid (AA) I being at the C-terminus of said peptide, and amino acid (AA) III through VIII, depending upon the number of amino acids present, being at the N-terminus of said peptide, to which substituent A is attached, but also including the peptide isostere component G, said peptide of Formula I being cyclical by virtue of a peptide bond between AA I and AA III or AA IV, comprising the steps of:

(A) treating an ester of the C-terminus amino acid (AA I) with the next adjacent amino acid (AA II) of said peptide, or peptide isostere component G, the amino group of said amino acid or isostere being protected by a protecting group, in the presence of a condensing agent, whereby a dipeptide of the two amino acids (AA I and II) or isostere G is formed;

(B) deprotecting the dipeptide formed in Step (A) by removing the protecting group form the amino group of AA II or isostere G;

(C) treating the dipeptide of AA I and AA II or isostere G with AA III, the amino group of which is protected by a protecting group, in the presence of a condensing agent, whereby a tripeptide of AA I, AA II and AA III is formed;

(D) deprotecting the tripeptide formed in Step (C) by removing the protecting group from the amino group of AA III to give the peptide of Formula I wherein A is hydrogen; the Steps (C) and (D) also optionally being carried out so as to introduce the peptide isostere component G;

(E) forming the methyl ester of AA I if said ester is not employed initially;

(F) cyclizing the tri- or tetrapeptide by forming a peptide bond between AA I and AA III or IV in the presence of a condensing agent to give the peptide of Formula I wherein A is hydrogen;

(G) treating the cyclical peptide formed in Step (F) with

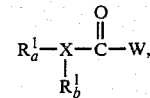

where X, $R_a^1$, and $R_b^1$, are as defined above and W is an acid halide, anhydride, or other carbonyl activating group, to give the peptide of Formula I wherein A is other than hydrogen; and optionally (H) forming a cyclical pentapeptide up to an octapeptide of AA I, through AA V-VIII, by repeating the procedure of Step (C) using protected AA V through protected AA VIII, followed by deprotecting of the pentapeptide through octapeptide to give the peptide of Formula I wherein A is hydrogen, and optionally treating the pentapeptide through octapeptide as in Step (G) above to give the peptide of Formula I wherein A is other than hydrogen; the step of cyclizing being carried out as recited in Steps (E) and (F) above, preferably after formation of the complete linear pentapeptide up to octapeptide, but optionally prior thereto, and also before or after formation of the A substituent; said method also comprising, where necessary, protection of sidechain substituents of the component amino acids AA I through AA VIII, with deprotection being carried out as a final step; said method also comprising any combination of the steps set out above, whereby the amino acids I through VIII and substituents A and G are assembled in any desired order to prepare the peptide of Formula I; said method also comprising employment of the steps set out above in a solid phase sequential synthesis, whereby in the initial step the carboxyl group of the selected amino acid is bound to a synthetic resin substrate while the amino group of said amino acid is protected, followed by removal of the protecting group, the succeeding steps being as set out above, the peptide as it is assembled being attached to said synthetic resin substrate; followed by a step of removing the peptide from said synthetic resin substrate by transesterification with methanol to give the methyl ester of AA I, followed by hydrolysis and cyclization as recited above; removal of sidechain protecting groups being accomplished either before or after removal of the peptide from said synthetic resin substrate; the steps of cyclization and formation of the A substituent in said method being accomplished at any time and in any order during preparation of peptides of different linear extent, after preparation of the minimal quadripeptide as recited above.

A preferred method involves preparation of the peptide of desired linear extent and desired A substituent by solid phase sequential synthesis, which is then removed by transesterification to give the linear, protected (N-terminus) methyl ester. The N-terminus protecting group, preferably benzyloxycarbonyl or chlorobenzyloxycarbonyl, is removed by catalytic hydrogenation, followed by hydrolysis of the methyl ester using potassium hydroxide in water and dioxane. Cyclization is then effected using diphenylphosporylazide in dimethylformamide, using triethylamine, diisopropylethylamine, or sodium bicarbonate as the base additive. Purification is accomplished by silica gel and/or sephadex gel chromatography.

The isostere component G of the novel peptides of the present invention may be prepared in accordance with well-known procedures in synthetic chemistry, as is described in more detail further below. Attachment of the isostere component G to the other components of the novel peptides of the present invention is carried out in the same manner as for any of said other components, and may involve addition of the isostere component in a protected form. For example, the following reactive groups would require such protection:

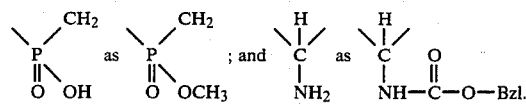

Such protecting groups may be removed as a final or near final step, for example, by base hydrolysis in the former case, or by hydrogenation in the latter.

Preparation of the particular isostere components may be carried out in accordance with procedures described below and in the literature cited particularly as follows:

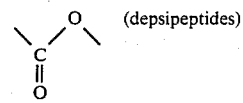

Ondetti et al., *Chemistry and Biology of Peptides*, ed. J. Meienhofer, Ann. Arbor Science pp. 525–531, 1972.

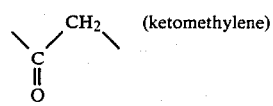

(1) Natarajan et al., Peptides. *Synthesis-Structure-Function*, ed. D. H. Rich and E. Gross, Pierce Chem. Co., Rockford, Ill., pp. 429–433, 1981.
(2) Van Lommen et al., European Peptide Symposium 16th, *Peptides* 1980, ed. K. Brunfeldt, Scriptor, Copenhagen, pp. 248–252, 1981.
(3) Almquist et al., *J. Med. Chem.*, 23: 1392–1398, 1980.

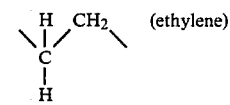

Kawasaki and Maeda, *Biochem. Biophys. Res. Comm.* 106: 113–116, 1982.

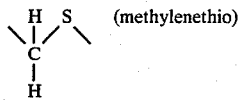

(1) Natarajan et al., Id.
(2) Fok and Yankellov, *Biochem. Biophys. Res. Comm.* 74: 273–278, 1977.
(3) Spatola et al., *Peptides. Structure-Function-Biological Function*, ed. E. Gross and J. Meienhofer, Pierce Chem. Co., Rockford, Ill., pp. 273–276, 1979.
(4) Spatola and Bettag, *J. Org. Chem.* 46: 2393–2394, 1981.

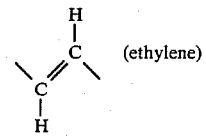

(1) Natarajan et al., Id.
(2) Hann et al., *J. Chem. Soc. Chem. Comm.*, 234–235, 1980.
(3) Cox et al., *J. Chem. Soc. Chem. Comm.*, 799–800, 1980.

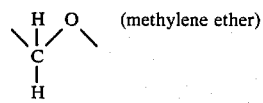

Ondetti et al., Id.

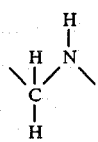 G. (methylene aza, or reduced isostere)

(1) Van Lommen et al., Id.
(2) Atherton et al., J. Chem. Soc. (C), 3393-3396, 1971.
(3) Parry et al., Chemistry and Biology of Peptides, ed. J. Meienhofer, Ann Arbor Science, pp. 541-544, 1972.
(4) Hudson et al., Int. J. Peptide Protein Res. 15: 122-129, 1979.
(5) Frank and Desiderio, Anal. Biochem. 90: 413-419, 1978.

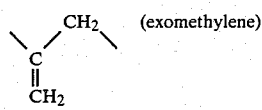 H. (exomethylene)

Prepared from ketomethylene by Wittig reaction.

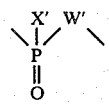 I.

(1) Jacobson and Bartlett, JACS 103: 654-657, 1981.
(2) Jennings-White and Almquist, Tet. Lett., 23: 2533-2534, 1982.
(3) Morton et al., Tet. Lett., 23: 4123-4126, 1982.

For example, the compound:

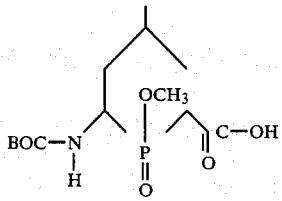

can be prepared in accordance with the following scheme:

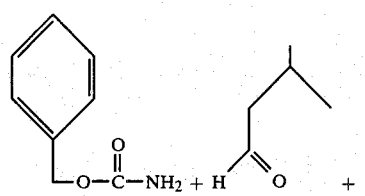

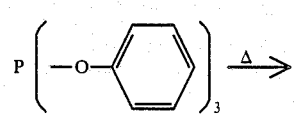

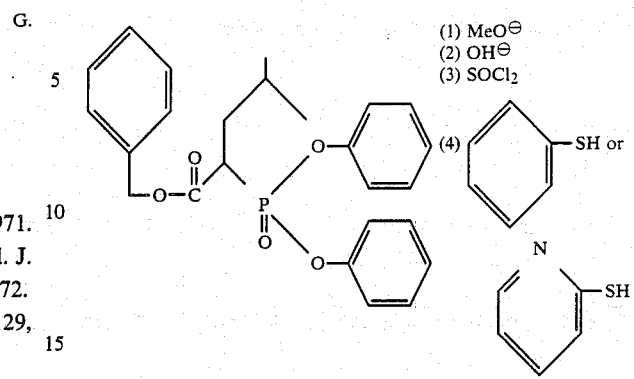

(1) MeO$^\ominus$
(2) OH$^\ominus$
(3) SOCl$_2$
(4)

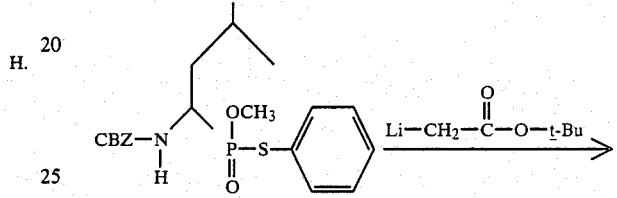

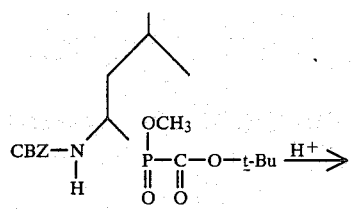

(III)

(mixture of two pairs of diastereomers; two isomers at *; active isomer indicated).

which can be incorporated into the synthesis for the overall peptide of the present invention, or converted to the α-BOC derivative by hydrogenation over Pd/C catalyst, followed by treatment with (BOC)$_2$O. Incorporation of (III.) or its BOC analog into a peptide sequence gives, after alkaline hydrolysis of the phosphinate ester, the free phosphinate

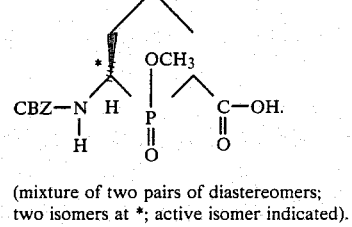

The product will contain two isomers at *; the active diastereomer has the relative configuration as an L amino acid, i.e., R-isomer in this case.

Also, the compound:

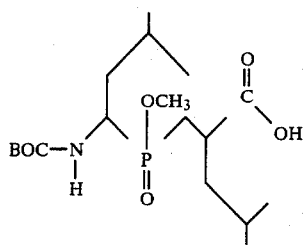

can be prepared in a fashion analgous to that described for (III.) above, for example from:

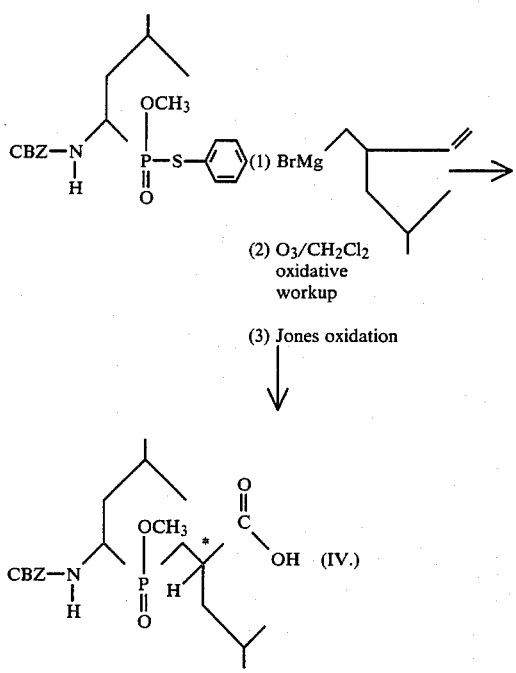

(active isomer shown; other isomers obtained as well)

Incorporation of (IV.) or its N-BOC analog proceeds as for (III.) above, with removal of the methyl phosphinate ester by hydrolysis (alkaline) to give the free phosphinate. The active isomer shown at * has the side chains in the relative configuration of the dipeptide that they mimic. For synthesis of

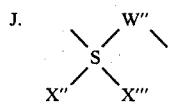
, see Jennings-White and Almquist, Id.

J. 
$$\begin{array}{c} W''' \\ | \\ X'' - S - X''' \end{array}$$

Morton et al., Id.

For example, the compound:

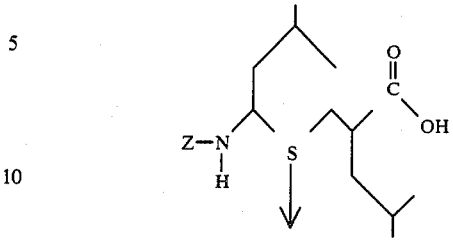

can be prepared in accordance with the following scheme:

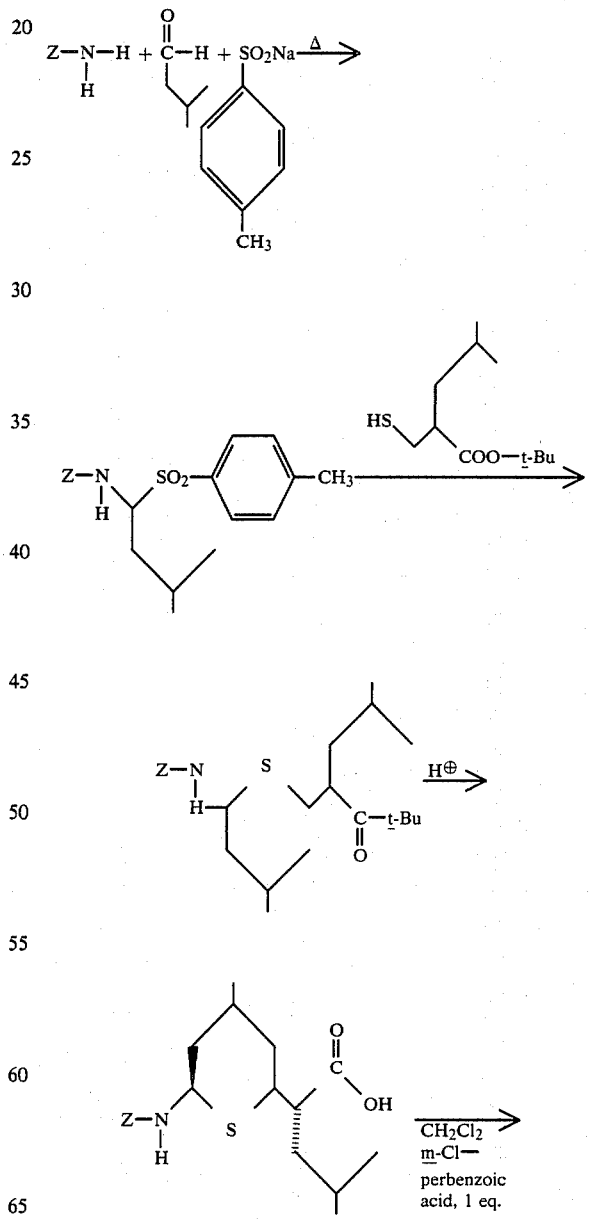

(one of the isomers obtained)

-continued

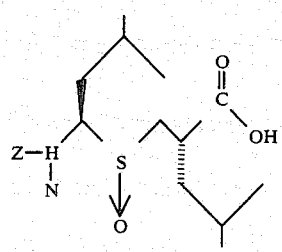

The sulfone

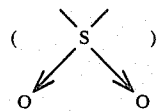

can be obtained using excess m-Cl-perbenzoic acid.
Use of

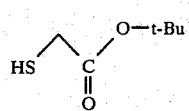

in the second step gives as the final product:

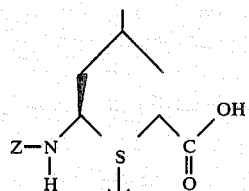

K.

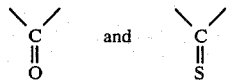

Prepared from the alcohol; see Rich et al., *Biochem. Biophys. Res. Comm.* 104: 1127–1133, 1982.

Conversion of the ketone to the thioketone is with use of:

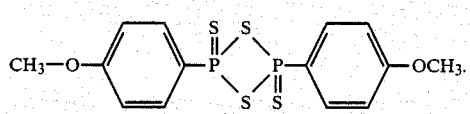

L.

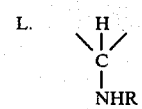

Obtained from

in accordance with the scheme outlined below; the R substituents are attached by conventional methods to the free amine (R=H):

Synthesis of protected 3-amino-3-deoxy-(3S,4S)-Statine:

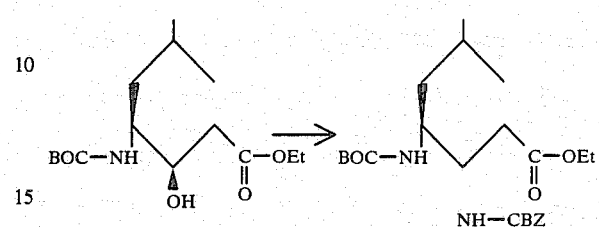

r.t.
pyridine
1-3 hr.

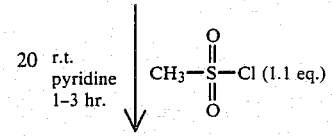

Evap., 35° C.
Pump 2-4 days

Aqueous workup
EtAc/10% citric acid (pre-shaken before dissolving up crude product)

Oiled out from EtAc/Hexane

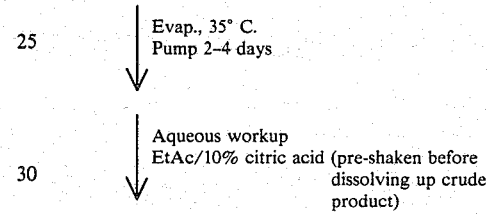

greater than 95% yield
greater than 95% purity
(TLC, NMR)

CDCl$_3$ | (nBU)$_4$N$^+$N$_3^-$
1 eq., 45° C., 18 hr.

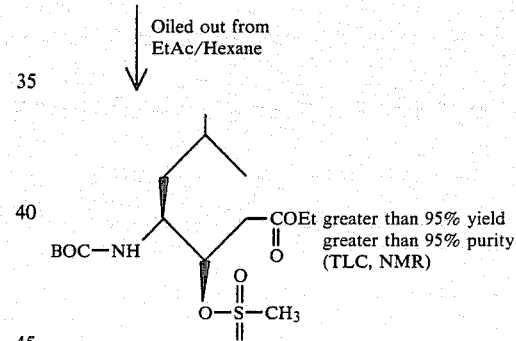

+ 20% elimination +
(nBu)$_4$N$^+$X

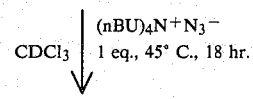

Aqueous workup

CHCl$_3$/EtOH | PtO$_2$/H$_2$
40 lbs., 4 hr.

100% elimination

-continued

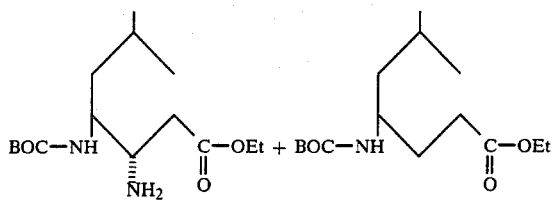

isolated by extraction into weak acid.

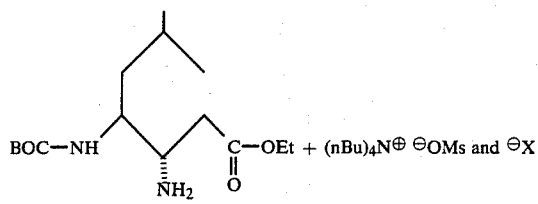

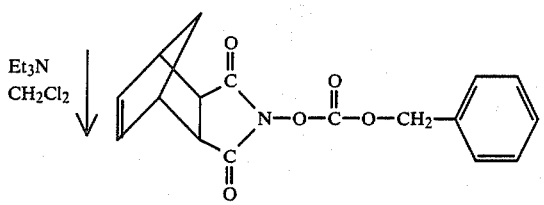

predominantly as shown

Base hydrolysis gives the free acid for incorporation into the synthesis of the overall peptides of the present invention.

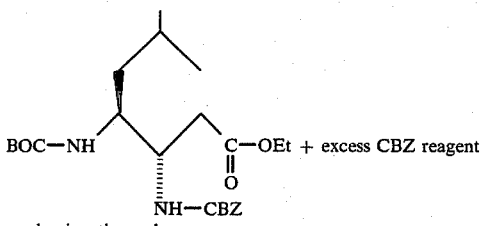 M.

Obtained from the amide according to the method described by Clausen et al., Seventh American Peptide Symposium, 1981:

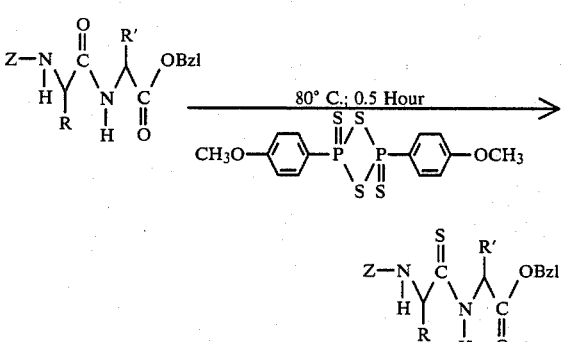

-continued

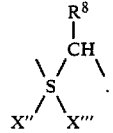 N.

(1) Natarajan et al., Id.
(2) Fok and Yankellov, Id.
(3) Spatola et al., Id.
(4) Spatola and Bettag, Id.
(5) Spatola et al., *Proceedings of the Seventh American Peptide Symposium*, ed. E. Gross and D. H. Rich, pp. 613–616, 1981.

The novel inhibitory peptides of the present invention are prepared by using the solid phase sequential synthesis technique.

In the following description several abbreviated designations are used for the amino acid components, certain preferred protecting groups, reagents and solvents. The meanings of such abbreviated designations are given below in Table I.

TABLE I

| Abbreviated Designation | |
|---|---|
| | Amino Acid |
| Ala | L-alanine |
| Arg | L-arginine |
| DAB | 2-$\underline{S}$—amino-4-aminobutyric acid |
| Gly | L-glycine |
| His | D or L-histidine |
| HLys | homolysine, 2$\underline{S}$—amino-6-amino-heptanoic acid |
| Ile | L-isoleucine |
| Leu | L-leucine |
| Lys | L-lysine |
| Met | L-methionine |
| Orn | L-ornithine |
| Phe | L-phenylalanine |
| Ser | L-serine |
| Sar | L-sarcosine (N—methylglycine) |
| Thr | L-threonine |
| Trp | L-tryptophan |
| Tyr | L-tyrosine |
| Val | L-valine |
| | Protecting Groups |
| BOC | tert-butyloxycarbonyl |
| CBZ | benzyloxycarbonyl |
| 2-Cl—CBZ | 2-chlorobenzyloxycarbonyl |
| IBU | iso-butyryl |
| IVA | iso-valeryl |
| DNP | dinitrophenyl |
| OMe | methyl ester |
| | Activating Groups |
| HBT | 1-hydroxybenzotriazole |
| | Condensing Agents |
| DCCI | dicyclohexylcarbodiimide |
| DPPA | diphenylphosphorylazide |
| | Reagents |
| TEA | triethylamine |
| TFA | trifluoroacetic acid |
| | Solvents |
| A | ammonium hydroxide (conc.) |
| AcOH | acetic acid |
| C | chloroform |
| DMF | dimethylformamide |
| E | ethyl acetate |
| M | methanol |
| P | pyridine |
| THF | tetrahydrofuran |
| W | water |

The synthesis of the peptides of the present invention by the solid phase technique is conducted in a stepwise

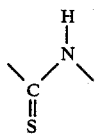

manner on chloromethylated resin. The resin is composed of fine beads (20-70 microns in diameter) of a synthetic resin prepared by copolymerization of styrene with 1-2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethylsubstituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as ONP ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyoxycarbonyl, and the like. It is preferred to utilize t-butyloxycarbonyl (BOC) for protecting the α-amino group in the amino acids undergoing reaction at the carboxyl end of said amino acid. The BOC protecting group is readily removed following such coupling reaction and prior to the subsequent step by the relatively mild action of acids (i.e. trifluoroacetic acid, or hydrogen chloride in ethyl acetate).

The OH group of Thr and Ser can be protected by the Bzl group and the —amino group of Lys can be protected by the INOC group or the 2-chlorobenzyloxycarbonyl (2-Cl-CBZ) group. Neither group is affected by TFA, used for removing BOC protecting groups. After the peptide is formed, the protective groups, such as 2-Cl-CBZ and Bzl, can be removed by treatment with HF or by catalytic hydrogenation.

After the peptide has been formed on the solid phase resin, it may be removed from the resin by a variety of methods which are well known in the art. For example the peptide may be cleaved from the resin with hydrazine, by ammonia in methanol, or by methanol plus a suitable base.

Preparation of the novel inhibitory peptides of the present invention utilizing the solid phase technique is illustrated in the following examples, which however, are not intended to be any limitation of the present invention.

EXAMPLE 1

L—Prolyl—L—Histidyl—L—Prolyl—L—Phenylalanyl—L—

Lysyl—L—Leucyl—L—Leucyl—L—Valeryl—L—Phenylalanyl

The peptide resin BOC-Pro-His-Pro-Phe-Lys-Leu-Leu-Val-Phe-O R was prepared by standard CBZ solid phase methods on a 2 mmole scale. Transesterification with methanol ad diisopropylethylamine (10%) 8 hours gave, after partitioning into n-butanol and washing with water, 1.76 g crude methyl ester, which was hydrogenated for 8 hours in ethanol containing a small amount of acetic acid and water, using 0.8 g Pd/C (10%) and 40 lbs hydrogen, to give, after filtration and evaporation of solvent, 1.91 g of crude epsilon-amino-Lys-containing ester. This ester was hydrolyzed in dioxane/water using sodium hydroxide to give approximately 2.0 g of crude BOC-Pro-His-Pro-Phe-Lys-Leu-Leu-Val-Phe, extracted into n-butanol at the approximate isoelectric point of the material. The crude material was cyclized using diphenylphosphoryl azide and sodium bicarbonate (both in excess) in dimethylformamide at 0° C. for 4 days. Evaporation and partitioning between n-butanol and water, washing with bicarbonate and with water, gave after evaporation of butanol 2.20 g of a butanol soluble residue. This crude material was $N^{\alpha}BOC$ deprotected using hydrochloric acid in ethyl acetate at −20° C. for 1 hour to five 1.45 g of an off-white solid after evaporation and drying. A 0.75 g portion was applied to a 50% acetic acid G-25 Sephadex column and the monomeric molecular weight material pooled, giving after precipitation from $CH_2Cl_2$/ether, 0.337 g material of $R_f=0.21$ in 80:10:1 chloroform:methanol:ammonium hydroxide (TLC). Fast Atom Bombardment mass spectrometry confirmed and proposed monomeric structure:

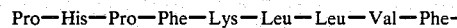

Pro—His—Pro—Phe—Lys—Leu—Leu—Val—Phe

HPLC: 91% pure. Amino Acid Analysis: $Pro_{1.01}His_{0.99}$-$Pro_{1.01}Phe_{0.98}Lys_{0.94}Leu_{1.02}Leu_{1.02}Val_{1.03}Phe_{0.98}$, 86% peptide content based on MW=1079.36. $^1H$ NMR (360 MHz): consistent with structure.

Elemental analysis: Calc'd for $$C_{57}H_{82}N_{12}O_9 \cdot C_2H_4O_2 \cdot 3H_2O$$
acetic acid
C, 59.37; H, 7.77; N, 14.00

Found: C, 59.68; H, 7.70; N, 13.65.

EXAMPLE 2

L—Prolyl—L—Histidyl—L—Prolyl—L—Phenylalanyl—L—

Lysyl—L—Phenylalanyl—L—Phenylalanyl—L—Valeryl—

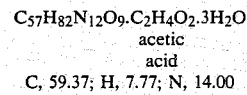

—L—Phenylalanyl

Prepared as described for Example 1 above to give 0.219 g monomeric material. TLC (80:10:1, chloroform:methanol:ammonium hydroxide): single spot $R_f=0.22$. MW 1147 confirmed by fast atom bombardment mass spectrometry. HPLC 92% pure. Amino acid analysis: $Pro_{1.03}His_{1.02}Pro_{1.03}Phe_{0.99}Lys_{0.96}Phe_{0.99}Phe_{0.9}$-$_9Val_{1.01}Phe_{0.99}$, 76% peptide based on MW=1146. 360 MHz $^1H$ NMR consistent with structure.

Elemental analysis: Calc'd for $C_{63}H_{78}N_{12}O_9 \cdot 2C_2H_4O_2 \cdot 7H_2O$ C, 57.75; H, 7.23; N, 12.06 Found: C, 58.04; H, 7.22; N, 11.69.

EXAMPLE 3 tert-Butyloxycarbonyl—L—Histidyl—L—Prolyl—L—Homophenylalanyl—L—Lysyl—(2S,4S,5S)—5-amino—6-cyclohexyl—4- hydroxy—2-isopropylhexanoyl—L—Isoleucyl—L—Histidyl

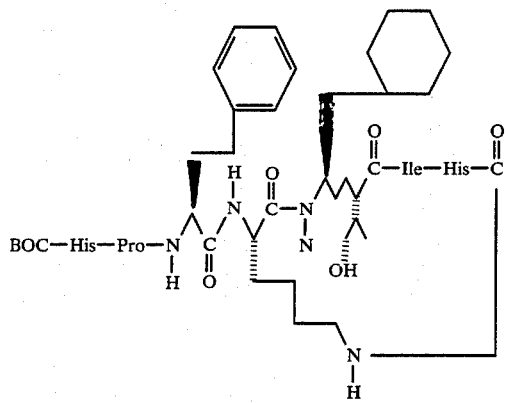

The title peptide is prepared by standard solid phase methodology as described in Erickson and Merrifield, *Proteins*, 3rd ed., 2: 257–527, 1976, using a Beckman Model 990B peptide synthesizer to carry out the operations according to the attached programs. Cyclization of the de-protected linear peptide is effected using diphenylphosphoryl azide in DMF containing and excess of sodium bicarbonate.

Step A tert-Butyloxycarbonyl-L-Histidyl-L-Prolyl-L-Homophenylalanyl-(N-2-chloro-benzyloxycarbonyl)-L-Lysyl-(2S,4S,5S)-5-amino-6-cyclohexyl-4-hydroxy-2-isopropylhexanoyl-L-Isoleucyl-L-Histidyl The starting polymer resin is BOC-(DNP)-His esterified to 2% cross-linking polystyrene-divinylbenzene (2 mmol, 1.65 g). The $N^\alpha$-BOC-derivatives of Ile, N-2-Cl-CBZ-Lys, L-HomoPhe, Pro, and His-DNP are coupled using dicyclohexylcarbodiimide with an equivalent of the additive 1-hydroxybenzotriazole hydrate. The BOC-group is removed with 40% trifluoroacetic acid. A coupling of 30 minutes followed by a recoupling of 60 minutes (2.5 equivalents each time of BOC-amino acid) are used for each amino acid, except for L-HomoPhe. These coupling times have been demonstrated previously to give complete coupling (as judged by the method of Kaiser) in this sequence. An additional recoupling of His is performed following Pro. In order to conserve the amounts of L-HomoPhe employed, an initial coupling using 1.25 equivalents of BOC-L-HomoPhe plus equal amounts of HBT and DCCI are stirred in the coupling step in 18 ml 1:1 DMF/CH₂Cl₂, for 6 hours, followed by a recouple of 6 hours using the same saved coupling solution, without the addition of more DCCI. This is found to give complete coupling. The N-terminal tert-butyloxycarbonyl group is coupled for 30 minutes as the symmetrical anhydride formed in situ from 5.0 equivalents of tert-butyric acid and 2.5 equivalents of DCCI (no HBT). This is followed by a recoupling similarly. The DNP protecting group of His is removed in the final program using two 25-minute treatments with 10% thiophenol in DMF. The finished resin peptide (3.2 g) is dried and suspended in 40 ml of dry methanol.

Step B tert-Butyloxycarbonyl-L-Histidyl-L-Prolyl-L-Homophenylalanyl-L-Lysyl-(2S,4S,5S)-5-amino-6-cyclohexyl-4-hydroxy-2-isopropylhexanoyl-L-Isoleucyl-Histidine To the suspension prepared in (A) above is added 10 ml diisopropylethylamine, and the reaction mixture is stirred under dry nitrogen for 18 hours. The mixture is then filtered and the resin beads washed with methanol and CH₂Cl₂. The yellow solution (combined all filtrates) is evaporated under reduced pressure to give crude methyl ester. This crude product is dissolved in 50 ml of methylene chloride containing 5 ml methanol and washed with water. The organic lower layer is dried over sodium sulfate and evaporated to give a yellow powder. This crude material can be purified on silica gel to give BOC-His-Pro-L-HomoPhe-(Cl-CBZ)-Lys-(2S,4S,5S)-5-amino-6-cyclohexyl-4-hydroxy-2-isopropylhexanoyl-L-Ile-His-OCH₃, but is most conveniently carried on to the next step without purification. Hydrolysis of the methyl ester is effected in 100 ml 1:1 dioxane (peroxide free), water, using 1N NaOH dripped in slowly over 3 hours. Evaporation of the dioxane and extraction of the aqueous layer with CH₂Cl₂ removes some impurities and yellow color from the aqueous layer, containing the peptide. Neutralization of the aqueous layer with an equivalent of 1N HCl, gives an oily precipitate, which is extracted into ethyl acetate, dried and evaporated to give the free acid. This material is dissolved in 30 ml ethanol containing 2 ml water and 1 ml acetic acid and hydrogenated on a Parr apparatus at 40 lbs. H₂ pressure using 0.2 g Pd/C catalyst for 5 hours. After TLC reveals the complete removal of the Cl-CBZ group, the solution is filtered through a Celite pad, and evaporated. The residue is dissolved in water (30 ml) and the pH adjusted to pH 6.5 with 0.1N NaOH, causing some precipitate to form. At this pH, the approximate isoelectric point for the Zwitterion product (the mean of the pKa's of the Lys-amine and His-carboxyl), the product can be cleanly extracted into n-butanol, which can be washed with water, and the n-butanol evaporated to give crude BOC-His-Pro-L-HomoPhe-Lys-(2S,4S,5S)-5-amino-6-cyclohexyl-4-hydroxy-2-isopropylhexanoyl-L-Ile-His-, B.

Step C tert-Butyloxycarbonyl—L—Histidyl—L—Prolyl—L—

Homophenylalanyl—L—Lysyl—(3S,4S,5S)—5-amino—6- cyclohexyl—4-hydroxy—2-isopropylhexanoyl—L—Ile—His

A 0.5 g portion (nominally 0.5 mmol) of the crude linear peptide, described in (B) is dissolved in 50 ml dry, degassed DMF in which 0.42 g (10 equivalents) of sodium bicarbonate is suspended. The solution is cooled to 0° C. and stirred. To this solution is added 0.41 g (0.323 mL) diphenylphosphoryl azide (3 equivalents) and the stirring continued for 48 hours. The solution is then evaporated, and the residue suspended in ethyl acetate and washed with water. The ethyl acetate layer is dried and evaporated to give the crude product residue which is dissolved in 50% acetic acid and applied to a Sephadex G-25 column packed in 50% acetic acid. Fractionation, primarily by molecular size, on this column gives a major peptide-containing peak, detected by ultraviolet spectroscopy at 210 nm, which proves to be monomeric material. This peak is collected and evaporated to give a moderately pure material as judged by TLC. Purification by silica gel chromatography (500 g silica; 0.04–0.063 mm particle size; 80:15:0.75:0.75, chloroform:methanol:water:acetic acid) gives a pure product after evaporation and precipitation from CH$_2$Cl$_2$/ether and drying. $^1$H NMR (360 MHz): spectrum is consistent with structure. Fast atom bombardment mass spectrometry confirms MW 997 as expected for the cyclic monomeric product.

| SCHEDULE OF STEPS FOR 6 MMOL RUN | | | |
|---|---|---|---|
| Step | Solvent/Reagent | Vol. (ml) | Mix time (min) |
| | Coupling Program 1 | | |
| 1 | CH$_2$Cl$_2$ | 6 × 60 | 2 |
| 2 | 40% TFA in CH$_2$Cl$_2$ | 1 × 60 | 2 |
| 3 | 40% TFA in CH$_2$Cl$_2$ | 1 × 60 | 25 |
| 4 | CH$_2$Cl$_2$ | 3 × 60 | 2 |
| 5 | 10% TEA in CH$_2$Cl$_2$ | 2 × 60 | 5 |
| 6 | CH$_2$Cl$_2$ | 3 × 60 | 2 |
| 7 | BOC-amino acid, HBT in 1:1 DMF/CH$_2$Cl$_2$ | 40 | 5 |
| 8 | 1.0 M DCCI in CH$_2$Cl$_2$ | 15 | 60 |
| 9 | DMF | 1 × 60 | 2 |
| 10 | MeOH | 2 × 60 | 2 |
| 11 | CH$_2$Cl$_2$ | 1 × 60 | 2 |
| | Re-Couple Program 2 | | |
| 1 | CH$_2$Cl$_2$ | 1 × 60 | 2 |
| 2 | 10% TEA in CH$_2$Cl$_2$ | 2 × 60 | 5 |
| 3 | CH$_2$Cl$_2$ | 3 × 60 | 2 |
| 4 | BOC-amino acid, HBT in 1:1 DMF/CH$_2$Cl$_2$ | 40 | 5 |
| 5 | 1.0 M DCCI in CH$_2$Cl$_2$ | 15 | 120 |
| 6 | DMF | 1 × 60 | 2 |
| 7 | MeOH | 2 × 60 | 2 |
| 8 | CH$_2$Cl$_2$ | 5 × 60 | 2 |
| | Program 3 (DNP removal) | | |
| 1 | CH$_2$Cl$_2$ | 1 × 60 | 2 |
| 2 | DMF | 2 × 60 | 2 |
| 3 | 10% phenylthiol in DMF | 1 × 60 | 25 |
| 4 | DMF | 1 × 60 | 2 |
| 5 | 10% TEA in CH$_2$Cl$_2$ | 1 × 60 | 2 |
| 6 | DMF | 2 × 60 | 2 |
| 7 | 10% phenylthiol in DMF | 1 × 60 | 25 |
| 8 | DMF | 3 × 60 | 2 |
| 9 | MeOH | 2 × 60 | 2 |
| 10 | CH$_2$Cl$_2$ | 2 × 60 | 2 |
| 11 | MeOH | 2 × 60 | 2 |
| 12 | CH$_2$Cl$_2$ | 2 × 60 | 2 |
| 13 | MeOH | 2 × 60 | 2 |

EXAMPLE 4–12

Following the standard solid phase methodology described above in Example 1, additional inhibitory peptides of the present invention are prepared. The peptides prepared are set out in the following table.

| Exp. No. | Peptide |
|---|---|
| 1. | Pro—His—Pro—Phe—Lys—Phe—Phe—Ile—His— |

| Exp. No. | Peptide |
|---|---|
| 2. | Pro—His—Pro—Phe—Lys—[Leu—Leu—]Residue Val—Phe— |
| 3. | Pro—His—Pro—Phe—Lys—[Leu—Val—]Residue Ile—His— |
| 4. | Pro—His—Pro—Phe— 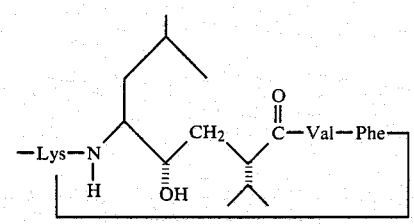 |
| 5. | Pro—His—Pro—Phe— 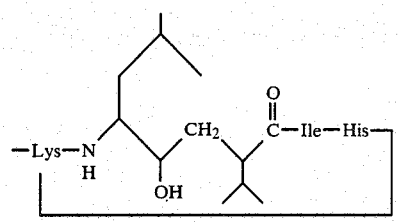 |
| 6. | BOC—Phe—Lys—[Leu—Val—]Residue Ile—His— |
| 7. | 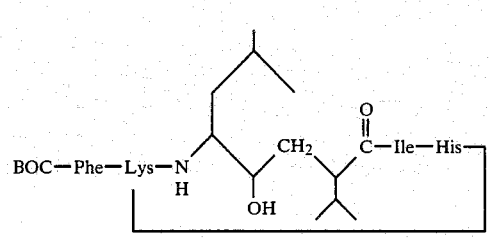 |
| | Pro—His—Pro—Phe— 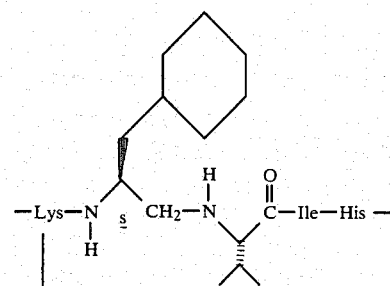 |

-continued

| Exp. No. | Peptide |
|---|---|

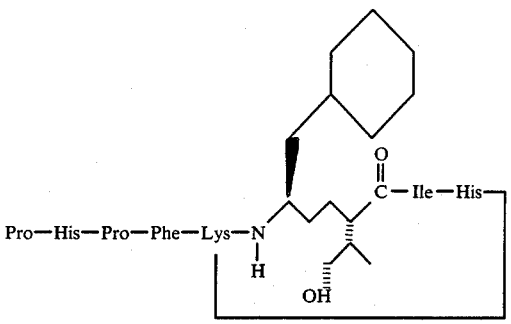

EXAMPLE 13

Hog Renin Inhibition

An assay was carried out in order to determine the inhibitory potency of the peptides of the present invention. The assay measured the inhibition of hog kidney renin, and was in accordance with the procedure described in Rich et al., *J. Med. Chem.* 23:27, 1980, except that a pH of 7.3 was used. The results of the assay, illustrated in the table below, are expressed as $I_{50}$ values, which refers to the concentration of peptide inhibitor necessary to produce 50% inhibition of renin activity. This $I_{50}$ value is obtained typically by plotting data from four inhibitor concentrations. Pepstatin was used as an active control.

| Peptide | $I_{50}(M)$ |
|---|---|
| BOC—Pro—His—Pro—Phe—<br>　　—Lys—Leu—Leu—Val—Phe⎤<br>　　└─────────────────────┘ | $1 \times 10^{-3}$ |
| Pro—His—Pro—Phe—<br>　　—Lys—Phe—Phe—Val—Phe⎤<br>　　└─────────────────────┘ | $1.8 \times 10^{-3}$ |

EXAMPLE 14

Human Renin Inhibition

An assay was carried out in order to determine the inhibitory potency of the peptides of the present invention. The assay measured the inhibition of human kidney renin purified as described in Bangham, D. R., Robertson, I., Robinson, J. I. S., Robinson, C. J., and Tree, M., *Clinical Science and Molecular Medicine*, 48 (Supp. 2): 136s–159s (1975), and further purified by affinity chromatography on pepstatin-aminohexyl-Sepharase as described in Poe, M., Wu., J. K., Florance, J. R., Radkey, J. A., Bennett, C. D., and Hoagsteen, K., *J. Biol. Chem.* (1982, in press). The assay was also in accordance with Poe et al. cited above. Results are expressed as $K_I$ values, which refer to the dissociation constant of the inhibited enzyme-inhibitor complex. This $K_I$ value was obtained as described above. Pepstatin was used as an active control. The results are set out in the table below.

| Peptide | $K_I(M)$ |
|---|---|
| BOC—Pro—His—Pro—Phe—<br>　　—Lys—Leu—Leu—Val—Phe⎤<br>　　└─────────────────────┘ | $6.4 \times 10^{-6}$ |
| Pro—His—Pro—Phe—<br>　　—Lys—Phe—Phe—Val—Phe⎤<br>　　└─────────────────────┘ | $3.3 \times 10^{-5}$ |

EXAMPLE 16

Preparation of

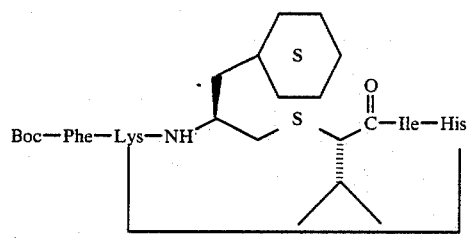

The peptide is assembled by solid phase and solution methods using methods similar to those described for Example 1, except that the dipeptide isostere (G) is prepared using procedures directly analogous to those described by S. Natarajan, et al., in *Peptides-Synthesis-Structure-Function*, who prepared the dipeptide isostere Z-NHCH(CH$_2$C$_6$H$_5$)—CH$_2$S—CH(CH$_3$)—COOH, beginning from Z-Phe, followed by reduction of the carboxyl with diborane and elaboration as outlined to the dipeptide isostere. In this case, the synthesis begins with Boc-L-Phe, which is reduced catalytically to Boc-L-Cyclohexylalanine, followed by reduction with diborane to the corresponding alcohol.

EXAMPLE 17

Preparation of

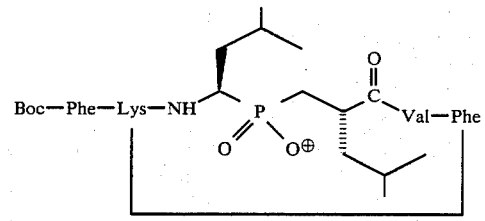

The peptide is assembled by solid phase and solution methods similar to those described for Example 1, except that the dipeptide isostere (G) is prepared as outlined on pp. 40–41 of this application. Free phosphinic acid is liberated as a final step by treatment with LiOH in THF/water.

What is claimed is:

1. A cyclic peptide of the formula:

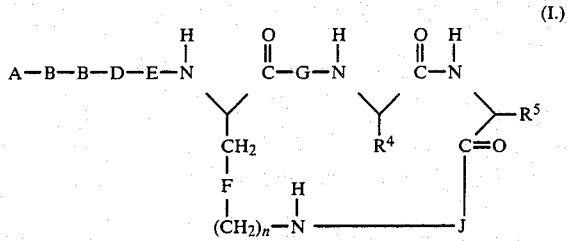 (I.)

wherein:
A is hydrogen or

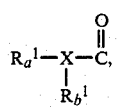

where
X is —O—, —O—CH—, —CH—O—, —CH—, —N-H—CH—, or —S—CH—; and
$R_a^1$ and $R_b^1$ may be the same or different and are hydrogen; W—$(CH_2)_p$— or W—$(CH_2)_{p'}$—CH=CH—$(CH_2)_{p''}$, where W is $C_1$-$C_4$-alkyl; hydrogen; phenyl; naphthyl; $C_3$-$C_7$-cycloalkyl; or $C_3$-$C_7$-cycloalkyl, phenyl or naphthyl substituted with up to five members independently selected from the group consisting of $C_1$-$C_8$-alkyl, trifluoromethyl, hydroxy, $C_1$-$C_4$-alkoxy, and halo;
p is 0 to 5; and p' and p" are independently 0 to 2; except that where X is —O—, only one of $R_a^1$ or $R_b^1$ is present;

B is absent, glycyl, sarcosyl, or

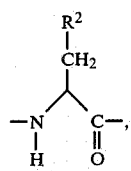

where $R^2$ is hydrogen; $C_1$-$C_4$-alkyl; hydroxy-$C_1$-$C_4$-alkyl; methylthiomethyl; indolyl; 4-imidazolyl; amino-$C_2$-$C_4$alkyl;

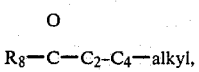

where $R^8$ is hydrogen, $C_1$-$C_4$-alkyl, hydroxy, or $C_3$-$C_7$-cycloalkyl; quanidyl-$C_2$-$C_3$-alkyl; or unsubstituted or mono- or disubstituted phenyl or naphthyl, where the substituent(s) is/are independently selected from the group consisting of $C_1$-$C_4$-alkyl, trifluoromethyl, hydroxy, $C_1$-$C_4$-alkoxy, and halo;
D is absent, —S— or

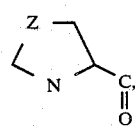

where Z is —$(CH_2)_m$— and m is 1 or 2;
E is absent or

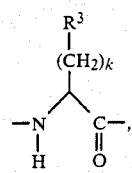

where k is 1 to 4; and $R^3$ is hydrogen; $C_1$-$C_4$-alkyl; indolyl; or unsubstituted or mono-, or disubstituted phenyl, naphthyl, phenyl-$C_1$-$C_4$-alkyl, or naphthyl-$C_1$-$C_4$-alkyl where the substituent(s) is/are independently selected from the group consisting of $C_1$-$C_4$-alkyl, trifluoromethyl, hydroxy, $C_1$-$C_4$-alkoxy, and halo;
F is absent, —$CH_2$—, —S—, or —O—;
n is 0 to 3;
G is

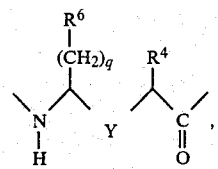

where $R^6$ is $C_3$-$C_6$-alkyl; or unsubstituted or mono-, or disubstituted $C_3$-$C_7$-cycloalkyl, phenyl or naphthyl, where the substituent(s) is/are independently selected from the group consisting of $C_1$-$C_4$-alkyl, trifluoromethyl, hydroxy, $C_1$-$C_4$-alkoxy, and halo; q is 1 to 4; $R^4$ is hydrogen; or

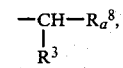

where $R^3$ is hydrogen; $C_1$-$C_4$-alkyl; indolyl; unsubstuted or mono-, or disubstituted phenyl, naphthyl, phenyl-$C_1$-$C_4$-alkyl, or naphthyl-$C_1$-$C_4$-alkyl, where the substituents(s) on the phenyl or naphthyl is/are independently selected from the group consisting of $C_1$-$C_4$alkyl,, trifluoromethyl, hydroxy, $C_1$-$C_4$alkoxy, and halo; and $R_a^8$ is hydrogen; $C_1$-$C_4$-alkyl; hydroxy; or $C_3$-$C_7$-cycloalkyl; and Y is

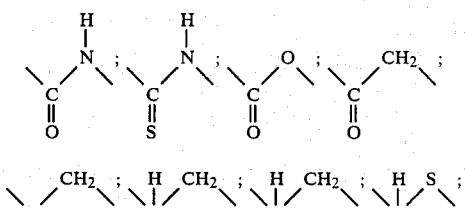

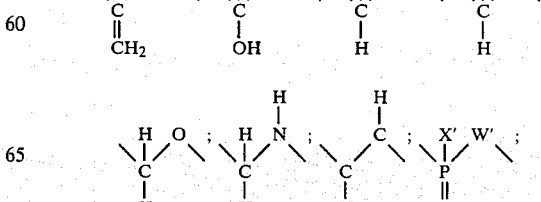

wherein X' is hydroxy; amino; or mono- or di-$C_1$–$C_4$-alkylamino; and W' is absent; —O—, —NH—, or —$CH_2$—;

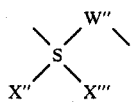

where X'' and X''' are independently absent or

and W''' is absent, —$CH_2$—, or

where $R^8$ is hydrogen or $C_1$–$C_3$-alkyl;

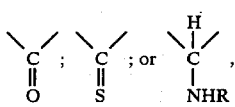

wherein R is hydrogen; $C_1$–$C_4$-alkyl; formyl; $C_1$–$C_4$-alkanoyl; phenoyl; $C_1$–$C_4$-alkoxy-carbonyl; or phenoxy-carbonyl; $R^5$ is hydrogen;

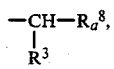

where $R^3$ and $R_a^8$ are as defined above; or —($CH_2$)-$_{n'}$—$R^9$, where n' is 0 to 4, and $R^9$ is guanidyl-$C_2$–$C_3$-alkyl; amino-$C_1$–$C_4$-alkyl; or an unsubstituted or mono or disubstituted heterocycle, wherein the heterocycle represents a 5- or 6- membered ring or benzofused 5- or 6-membered ring, where the one or two heteroatoms are independently selected from N, O, S, NO, SO, or quaternized N, and the substitutent(s) is/are independently selected from the group consisting of $C_1$–$C_6$alkyl, hydroxy, trifluoromethyl, $C_1$–$C_4$alkoxy, halo, phenyl, naphthyl, phenyl-$C_1$–$C_4$-alkyl, naphthyl-$C_1$–$C_4$-alkyl, amino, and mono- or di-$C_1$–$C_4$-alkylamino;

J is absent or glycyl; and wherein all of the asymmetric carbon atoms have an S configuration, except for those in the B, D and Y portion of G substituents, which may have either an S or an R configuration; and pharmaceutically-acceptable salts thereof.

2. A cyclic peptide according to claim 1 selected from the group consisting essentially of:

Pro—His—Pro—Phe—Lys—Phe—Phe—Val—Phe

Pro—His—Pro—Phe—Lys—Phe—Phe—Ile—His

Pro—His—Pro—Phe—Lys— Residue [Leu—Leu—] Val—Phe

-continued

Pro—His—Pro—Phe—Lys— Residue [Leu—Val—] Ile—His

Pro—His—Pro—Phe—Lys— Residue [Leu—Val—] Ile—His

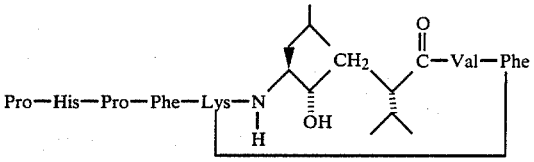

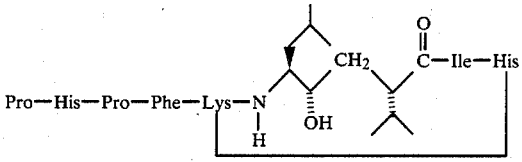

BOC—Phe—Lys— Residue [Leu—Val—] Ile—His

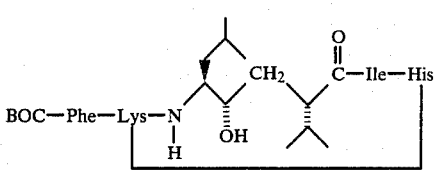

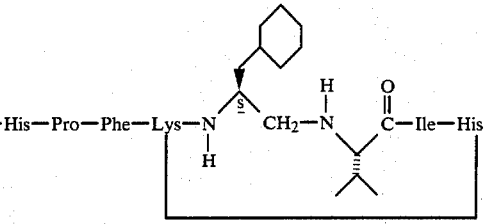

3. A pharmaceutical composition for treating renin-associated hypertension or renin-associated hyperaldosteronism, comprising a pharmaceutical carrier and a therapeutically-effective amount of a cyclic peptide or pharmaceutically-acceptable salt thereof according to claim 1.

4. A pharmaceutical composition according to claim 3, wherein the cyclic peptide is a member selected from the group consisting essentially of:

Pro—His—Pro—Phe—Lys—Phe—Phe—Val—Phe

Pro—His—Pro—Phe—Lys—Phe—Phe—Ile—His

Pro—His—Pro—Phe—Lys— Residue [Leu—Leu—] Val—Phe

-continued

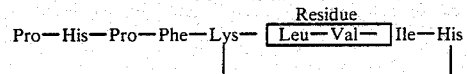

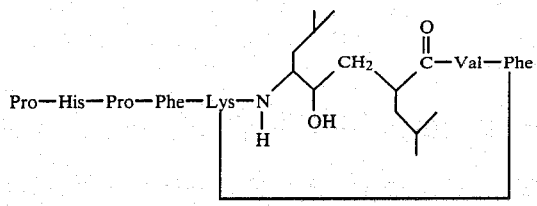

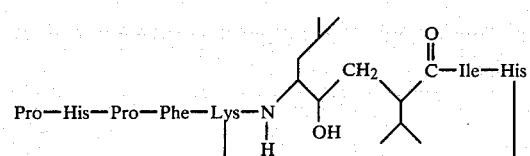

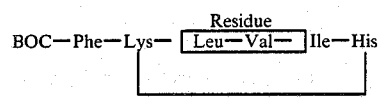

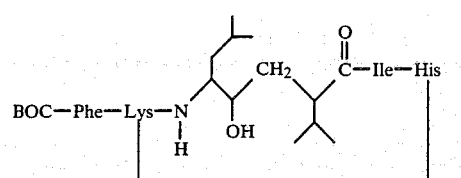

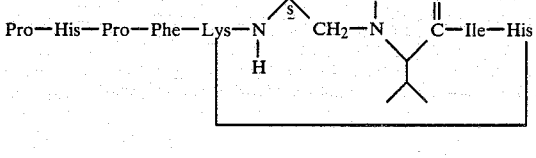

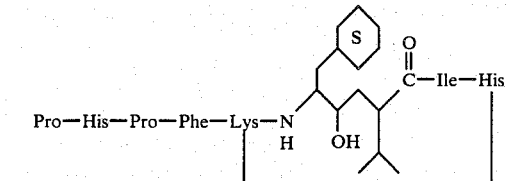

5. A method of treating renin-associated hypertension or renin-associated hyperaldosteronism, comprising administering to a patient in need of such treatment, a therapeutically effective amount of a cyclic peptide or pharmaceutically-acceptable salt thereof according to claim 1.

6. A method according to claim 5, wherein the cyclic peptide is a member selected from the group consisting essentially of:

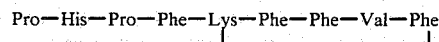

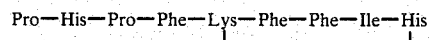

-continued

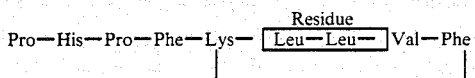

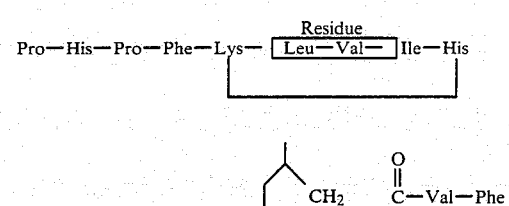

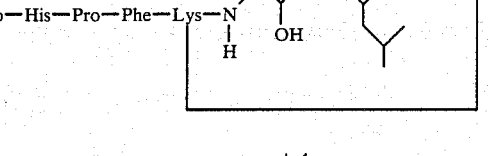

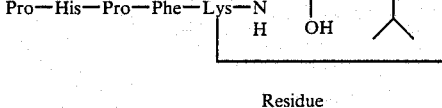

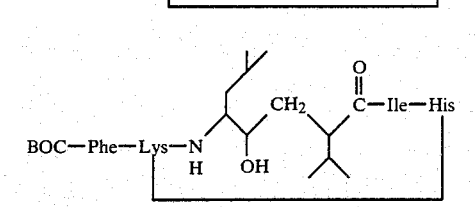

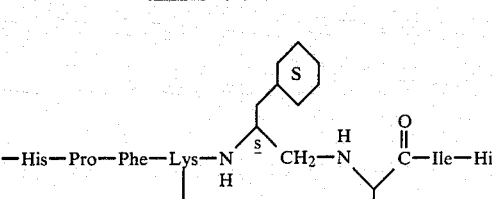

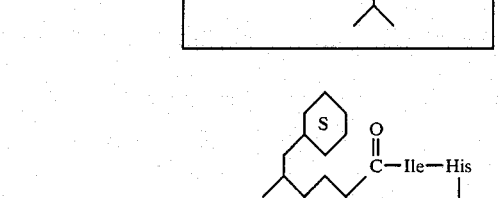

7. A method of determining the presence of renin-associated hypertension in a patient, comprising administering to such a patient, in a single dose at a hypotensive dosage level, a cyclic peptide or pharmaceutically-acceptable salt thereof according to claim 1, followed by monitoring of the blood pressure of the patient, with a transitory fall in the patient's blood pressure indicating supranormal plasma renin levels in the patient.

8. A composition for treating hypertension comprising a cyclic peptide or pharmaceutically-acceptable salt thereof according to claim 1. and one or more antihypertensive agents selected from the group consisting essentially of:

Diuretics: acetazolamide; amiloride; bendroflumethiazide; benzthiazide; bumetanide; chlorothiazide; chlorthalidone; cyclothiazide; ethacrynic acid; furosemide; hydrochlorothiazide; hydroflumethiazide; indacrinone (racemic mixture, or as either the (+) or (−) enantiomer alone, or a manipulated ratio, e.g., 9:1 of said enantiomers, respectively); metolazone; methyclothiazide; muzolimine; polythiazide; quinethazone; sodium ethacrynate; sodium nitroprusside; spironolactone; tricrynafen; triamterene; trichlormethiazide;

α-Adrenergic Blocking Agents: dibenamine; phentolamine; phenoxybenzamine; prazosin; tolazoline;

β-Adrenergic Blocking Agents: atenolol; metoprolol; nadolol; propranolol; timolol; ((±)-2-[3-(tert-butylamino)-2-hydroxypropoxy]-2-furan-anilide) (ancarolol);
(2-acetyl-7-(2-hydroxy-3-isopropylaminopropoxy)benzofuran HCl) (befunolol);
((±)-1-(isopropylamino)-3-(p-(2-cyclopropylmethoxyethyl)-phenoxy)-2-propranol HCl) (betaxolol);
(1-[(3,4-dimethoxyphenethyl)amino]-3-(m-tolyloxy)-2-propanol HCl) (bevantolol);
(((±)-1-(4-((2-isopropoxyethoxy)methyl)phenoxy)-3-isopropylamino-2-propanol)fumarate) (bisoprolol);
(4-(2-hydroxy-3-[4-(phenoxymethyl)-piperidino]-propoxy)-indole);
(carbazolyl-4-oxy-5,2-(2-methoxyphenoxy)-ethylamino-2-propanol);
(1-((1,1-dimethylethyl)amino)-3-((2-methyl-1H-indol-4-yl)oxy)-2-propanol benzoate) (bopindolol);
(1-(2-exobicyclo[2.2.1]-hept-2-ylphenoxy)-3-[(1-methylethyl)- amino-2-propanol HCl) (bornaprolol);
(o-[2-hydroxy-3-[(2-indol-3-yl-1,1-dimethylethyl)amino]propoxy]benzonitrile HCl) (bucindolol);
(α-[(tert.butylamino)methyl]-7-ethyl-2-benzofuranmethanol) (bufuralol);
(3-[3-acetyl-4-[3-(tert.butylamino)-2-hydroxypropyl]-phenyl]-1,1-diethylurea HCl) (celiprolol);
((±)-2-[2-[3-[(1,1-dimethylethyl)amino]-2-hydroxypropoxy]phenyl]-N-methylacetamide HCl) (cetamolol);
(2-benzimidazolyl-phenyl(2-isopropylaminopropanol));
((±)-3'-acetyl-4'-(2-hydroxy-3-isopropylaminopropoxy)acetanilide HCl) (diacetolol);
(methyl-4-[2-hydroxy-3-[(1-methylethyl)aminopropoxy]]benzenepropanoate HCl) (esmolol);
(erythro-DL-1-(7-methylindan-4-yloxy)-3-isopropylaminobutan-2-ol);
(1-(tert.butylamino)-3-[O-(2-propynyloxy)phenoxy]-2-propanol (pargolol);
(1-(tert.butylamino)-3-[o-(6-hydrazino-3-pyridazinyl)-phenoxy]-2-propanol diHCl) (prizidilol);
((−)-2-hydroxy-5-[(R)-1-hydroxy-2-[(R)-(1-methyl-3-phenylpropyl)amino]ethyl]benzamide);
(4-hydroxy-9-[2-hydroxy-3-(isopropylamino)-propoxy]-7-methyl-5H-furo[3,2-g][1]-benzopyran-5-one) (iprocrolol);
((−)-5-(tert.butylamino)-2-hydroxypropoxy]-3,4-dihydro-1-(2H)-naphthalenone HCl) (levobunolol);
(4-(2-hydroxy-3-isopropylamino-propoxy)-1,2-benzisothiazole HCl);
(4-[3-(tert.butylamino)-2-hydroxypropoxy]-N-methylisocarbostyril HCl);
((±)-N-2-[4-(2-hydroxy-3-isopropyl aminopropoxy)-phenyl]ethyl-N'-isopropylurea) (pafenolol);

(3-[[(2-trifluoroacetamido)ethyl]amino]-1-phenoxypropan-2-ol);
(N-(3-(o-chlorophenoxy)-2-hydroxypropyl)-N'-(4'-chloro2,3-dihydro-3-oxo-5-pyridazinyl)ethylenediamine);
((±)-N-[3-acetyl-4-[2-hydroxy-3-[(1-methylethyl)amino]-propoxy]phenyl]butanamide) (acebutolol);
((±)-4'-[3-(tert-butylamino)-2-hydroxypropoxy]spiro[cyclohexane-1,2'-indan]-1'-one) (spirendolol); (7-[3-[[2-hydroxy-3-[(2-methylindol-4-yl)oxy]propyl]amino]butyl]thiophylline) (teoprolol);
((±)-1-tert.butylamino-3-(thiochroman-8-yloxy)-2-propanol) (tertatolol);
((±)-1- tert.butylamino-3-(2,3-xylyloxy)-2-propanol HCl) (xibenolol);
(8-[3-(tert-butylamino)-2-hydroxypropoxy]-5-methyl-coumarin) (bucumolol);
(2-(3-(tert-butylamino)-2-hydroxy-propoxy)benzonitrile HCl) (bunitrolol);
((±)-2'-[3-(tert-butylamino)-2-hydroxypropoxy-5'-fluorobutyrophenone](butofilolol);
(1-(carbazol-4-yloxy)-3-(isopropylamino)-2-propanol) (carazolol);
(5-(3-tert.butylamino-2-hydroxy)propoxy-3,4-dihydrocarbostyril HCl) (carteolol);
(1-(tert.butylamino)-3-(2,5-dichlorophenoxy)-2-propanol) (cloranolol);
(1-(inden-4(or 7)-yloxy)-3-(isopropylamino)-2-propanol HCl) (indenolol);
(1-isopropylamino-3-[(2-methylindol-4-yl)oxy]-2-propanol) (mepindolol);
(1-(4-acetoxy-2,3,5-trimethylphenoxy)-3-isopropylaminopropan-2-ol) (metipranolol);
(1-(isopropylamino)-3-(o-methoxyphenoxy)-3-[(1-methylethyl)amino]-2-propanol) (moprolol);
((1-tert.butylamino)-3-[(5,6,7,8-tetrahydro-cis-6,7-dihydroxy-1-naphthyl)oxy]-2-propanol) (nadolol);
((S)-1-(2-cyclopentylphenoxy)-3-[(1,1-dimethylethyl)-amino]-2-propanol sulfate (2:1)) (penbutolol);
(4'-[1-hydroxy-2-(amino)ethyl]methanesulfonanilide) (sotalol);
(2-methyl-3-[4-(2-hydroxy-3-tert.butylaminopropoxy)-phenyl]-7-methoxy-isoquinolin-1-(2H)-one);
(1-(4-(2-(4-fluorophenyloxy)ethoxy)phenoxy)-3-isopropylamino-2-propanol HCl);
((−)-p-[3-[(3,4-dimethoxyphenethyl)amino]-2-hydroxypropoxy]-β-methylcinnamonitrile) (pacrinolol);
((±)-2-(3'-tert.butylamino-2'-hydroxypropylthio)-4-(5'-carbamoyl-2'-thienyl)thiazole HCl) (arotinolol);
((±)-1-[p-[2-(cyclopropylmethoxy)ethoxy]phenoxy]-3-(isopropylamino)-2-propanol) (cicloprolol);
((±)-1-[(3-chloro-2-methylindol-4-yl)oxy]-3-[(2-phenoxyethyl)amino]-2propanol) (indopanolol);
((±)-6-[[2-[[3-(p-butoxypheboxy)-2-hydroxypropyl]amino]ethyl]amino]-1,3-dimethyluracil) (pirepolol);
(4-(cyclohexylamino)-1-(1-naphtholenyloxy)-2-butanol);
(1-phenyl-3-[2-[3-(2-cyanophenoxy)-2-hydroxypropyl]-aminoethyl]hydantoin HCl);
(3,4-dihydro-8-(2-hydroxy-3-isopropylaminopropoxy)-3-nitroxy-2H-1-benzopyran) (nipradolol);

α and β-Adrenergic Blocking Agents:
((±)-1-tert-butylamino-3-[o-[2-(3-methyl-5-isoxazolyl)vinyl]phenoxy]-2-propanol) (isoxaprolol);
(1-isopropylamino-3-(4-(2-nitroxyethoxy)phenoxy)-2-propanol HCl);

(4-hydroxy-α-[[3-(4-methoxyphenyl)-1-methylpropyl]aminomethyl]-3-(methylsulfinyl)-benzmethanol HCl) (sulfinalol);

(5-[1-hydroxy-2-[[2-(o-methoxyphenoxy)ethyl]amino]ethyl]-2-methylbenzenesulfonamide HCl);

(5-[1-hydroxy-2-[(1-methyl-3-phenylpropyl)amino]ethyl]salicylamide HCl) (labetalol);

(1-((3-chloro-2-methyl-1H-indol-4-yl)oxy)-3-((2-phenoxyethyl)amino)-2-propanol- hydrogenmalonate) (ifendolol);

(4-(2-hydroxy-3-[(1-methyl-3-phenylpropyl)amino]-propoxy)benzeneacetamide);

(1-[3-[[3-(1-naphthoxy)-2-hydroxypropyl]-amino]-3,3-dimethyl-propyl]-2-benzimidazolinone);

(3-(1-(2-hydroxy-2-(4-chlorophenylethyl)-4-piperidyl)-3,4-dihydroxy)quinoxolin-2(1H)-one);

CNS-Acting Agents: clonidine; methyldopa;

Adrenergic Neuron Blocking Agents: quanethidine; reserpine and other rauwolfia alkaloids such as rescinnamine;

Vasodilators: diazoxide; hydralazine; minoxidil;

Angiotensin I Converting Enzyme Inhibitors:

1-(3-mercapto-2-methyl-1-oxopropyl)-L-proline (captopril);

(1-(4-ethoxycarbonyl-2,4(R,R)-dimethylbutanoyl)indoline-2(S)-carboxylic acid);

(2-[2-[[1-(ethoxycarbonyl)-3-phenyl-propyl]amino]-1-oxopropyl]-1,2,3,4-tetrahydro-3-isoquinoline carboxylic acid);

((S)-1-[2-[[1-(ethoxycarbonyl)-3-phenylpropyl]amino]-1-oxopropyl]octahydro-1H-indole-2-carboxylic acid HCl);

(N-cyclopentyl-N-(3-(2,2-dimethyl-1-oxopropyl)thiol-2-methyl-1-oxopropyl)glycine) (pivalopril);

((2R,4R)-2-(2-hydroxyphenyl)-3-(3-mercaptopropionyl)-4-thiazolidinecarboxylic acid)

(1-(N-[1(S)-ethoxycarbonyl-3-phenylpropyl]-(S)-alanyl)cis, syn-octahydroindol-2(S)-carboxylic acid HCl);

((−)-(S)-3-mercapto-2-methyl-1-oxopropyl]indoline-2-carboxylic acid);

([1(S),4S]-1-[3-(benzoylthio)-2-methyl-1-oxopropyl]-4-phenylthio-L-proline;

(3 -([1-ethoxycarbonyl-3-phenyl-(1S)-propyl]amino)-2,3,4,5-tetrahydro-2-oxo-1-(3S)-benzazepine-1-acetic acid HCl);

(N-(2-benzyl-3-mercaptopropanoyl)-S-ethyl-L-cysteine) and the S-methyl analogue;

(N-(1(S)-ethoxycarbonyl-3-phenylpropyl)-L-alanyl-L-proline maleate) (enalapril);

N-[1-(S)-carboxy-3-phenylpropyl]-L-alanyl-1-proline;

N²-[1-(S)-carboxy-3-phenylpropyl]-L-lysyl-L-proline (lysinopril);

Other Antihypertensive Agents: aminophylline; cryptenamine acetates and tannates; deserpidine; meremethoxylline procaine; pargyline; trimethaphan camsylate; including pharmaceutical salt and ester forms thereof.

9. A method according to claim 7, wherein the hypotensive dosage level is from 0.1 to 10 mg per kg of body weight, and the cyclic peptide or pharmaceutically-acceptable salt thereof is administered by intravenous injection.

* * * * *